United States Patent
Bakos et al.

(10) Patent No.: US 10,555,735 B2
(45) Date of Patent: Feb. 11, 2020

(54) TISSUE COMPRESSION ASSEMBLIES WITH BIODEGRADABLE INTERLINKS

(71) Applicant: ETHICON LLC, Guaynabo, PR (US)

(72) Inventors: Gregory J. Bakos, Mason, OH (US); Nicholas B. Van Stolk, Cincinnati, OH (US); Mark S. Ortiz, Milford, OH (US); John Burke, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 329 days.

(21) Appl. No.: 15/419,171

(22) Filed: Jan. 30, 2017

(65) Prior Publication Data
US 2018/0214153 A1   Aug. 2, 2018

(51) Int. Cl.
*A61B 17/11*   (2006.01)
*A61B 17/00*   (2006.01)

(52) U.S. Cl.
CPC . *A61B 17/1114* (2013.01); *A61B 2017/00818* (2013.01)

(58) Field of Classification Search
CPC ............... A61B 17/11; A61B 17/1114; A61B 2017/00876; A61B 2017/0456; A61B 2017/0458; A61B 2017/1117; A61B 2017/1139; A61B 17/08; A61B 17/083; A61B 17/12; A61B 17/122; A61B 2017/081; A61B 2017/1103; A61B 2017/1107; A61B 2017/111; A61B 2017/1121; A61B 2017/1132; A61B 2017/1135; F16G 11/105; F16G 11/106
See application file for complete search history.

(56) References Cited

U.S. PATENT DOCUMENTS

| | | |
|---|---|---|
| 6,171,320 B1 | 1/2001 | Monassevitch |
| 7,445,622 B2 | 11/2008 | Ortiz et al. |
| 7,637,919 B2 | 12/2009 | Ishikawa et al. |
| 7,780,686 B2 | 8/2010 | Park et al. |

(Continued)

OTHER PUBLICATIONS

International Search Report and Written Opinion dated Aug. 13, 2018 for Application No. PCT/IB2018/050352, 17 pgs.

(Continued)

*Primary Examiner* — Diane D Yabut
(74) *Attorney, Agent, or Firm* — Frost Brown Todd LLC

(57) ABSTRACT

Devices are used to modify a metabolic pathway of a digestive system by creating a pathway within the intestinal tract through an anastomosis between a proximal location within the intestinal tract and a distal location within the intestinal tract. A magnetic anastomosis compression device includes a first arm, a second arm, a resilient member, and a pair of magnets. The magnetic anastomosis compression device further includes a degradable retaining element. The retaining element temporarily holds the first arm and second arm in a wide configuration in opposition to the bias exerted by the resilient member. Upon the degradation of the retaining element, the resilient member causes the first arm and second arm to transition to a narrow configuration. The magnetic anastomosis compression device is configured to magnetically couple with another magnetic anastomosis compression device positioned within a different location within the intestinal tract.

20 Claims, 11 Drawing Sheets

(56) References Cited

U.S. PATENT DOCUMENTS

| | | |
|---|---|---|
| 7,907,549 B2 | 3/2011 | Colven et al. |
| 8,142,454 B2 | 3/2012 | Harrison et al. |
| 8,197,498 B2 | 6/2012 | Coleman et al. |
| 8,684,995 B2 | 4/2014 | Sato et al. |
| 8,828,031 B2 | 9/2014 | Fox et al. |
| 8,828,032 B2 | 9/2014 | McWeeney et al. |
| 8,864,781 B2 | 10/2014 | Surti et al. |
| 8,870,898 B2 | 10/2014 | Beisel et al. |
| 8,870,899 B2 | 10/2014 | Beisel et al. |
| 9,364,238 B2 | 6/2016 | Bakos et al. |
| 9,381,041 B2 | 7/2016 | Brown et al. |
| 9,456,820 B2 | 10/2016 | Ganger et al. |
| 2006/0036267 A1 | 2/2006 | Saadat et al. |
| 2009/0048618 A1* | 2/2009 | Harrison ............ A61B 17/0483 606/153 |
| 2010/0063520 A1* | 3/2010 | Bilotti ................. A61B 17/1114 606/153 |
| 2011/0137394 A1 | 6/2011 | Lunsford et al. |
| 2013/0253550 A1* | 9/2013 | Beisel ................. A61B 17/1114 606/153 |
| 2014/0309670 A1* | 10/2014 | Bakos ................. A61B 17/1114 606/153 |
| 2016/0324523 A1 | 11/2016 | Lukin et al. |
| 2017/0035425 A1 | 2/2017 | Fegelman et al. |

OTHER PUBLICATIONS

U.S. Appl. No. 61/697,845, filed Sep. 7, 2012.

Ryou, M. et al, "Endoscopic Intestinal Bypass Creation by Using Self-Assembling Magnets in a Porcine Model" Gastrointestinal Endoscopy, vol. 83, No. 4, pp. 821-825, 2016.

Ryou, M. et al, "Minimally Invasive Entero-Enteral Dual-Path Bypass Using Self-Assembling Magnets" Surgical Endoscopy, Springer Feb. 19, 2016.

* cited by examiner

TISSUE COMPRESSION ASSEMBLIES WITH BIODEGRADABLE INTERLINKS

BACKGROUND

In some instances, it may be desirable to provide a side-to-side anastomosis between two naturally occurring lumens within a patient's body. By way of example only, it may be desirable to provide an anastomosis between two portions of a patient's gastrointestinal tract, such as between the patient's duodenum and the patient's ileum. In some patients, it may improve glucose control, serve as a treatment for type 2 diabetes, and/or provide other results when the jejunum is diverted by an anastomosis. In such a procedure, a first enterotomy may be formed in the sidewall of the duodenum while a second enterotomy is formed in the sidewall of the ileum. The sidewalls may then be positioned adjacent to each other to form an anastomosis between the portions of the duodenum and the ileum in which the enterotomies are formed, as described in greater detail below. The anastomosis establishes direct fluid communication between the adjacent portions of the duodenum and ileum, enabling at least some nutrient-rich chyme to pass through the anastomosis to travel from the duodenum directly to the ileum without passing through the jejunum. In other variations in which the anastomosis is positioned at other locations within the gastrointestinal tract, some chyme may pass through a shortened portion of the jejunum. In either case, the anastomosis enables accelerated passage of nutrient-rich chyme through the gastrointestinal tract.

One or more devices may be positioned within the first and second enterotomies to hold the sidewalls of the duodenum and ileum together, thereby holding the first and second openings in alignment with each other and maintaining patency through the openings. The device or devices may compress the tissue, which may ultimately result in a serosa-to-serosa adhesion that secures the duodenum sidewall to the ileum sidewall. In addition, tissue captured in the device or devices may eventually necrose, such that the device or devices is/are eventually released into the gastrointestinal tract and subsequently passed through the bowels. Traditional examples of anastomosis devices include Denan's rings and the Murphy button. Examples of anastomosis procedures and associated devices are taught in U.S. Provisional Patent App. No. 61/697,845, entitled "Magnetic Compression Anastomosis Device," filed Sep. 7, 2012, the disclosure of which is incorporated by reference herein; U.S. Pat. No. 9,364,238, entitled "Method and Apparatus for Joining Hollow Organ Sections in Anastomosis," issued Jun. 14, 2016, the disclosure of which is incorporated by reference herein; and U.S. patent application Ser. No. 15/298,816, entitled "Method for Partial Diversion of the Intestinal Tract," filed Oct. 20, 2016, published as U.S. Pub. No. 2017/0035425 on Feb. 9, 2017, the disclosure of which is incorporated by reference herein.

While a variety of anastomosis devices and methods have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
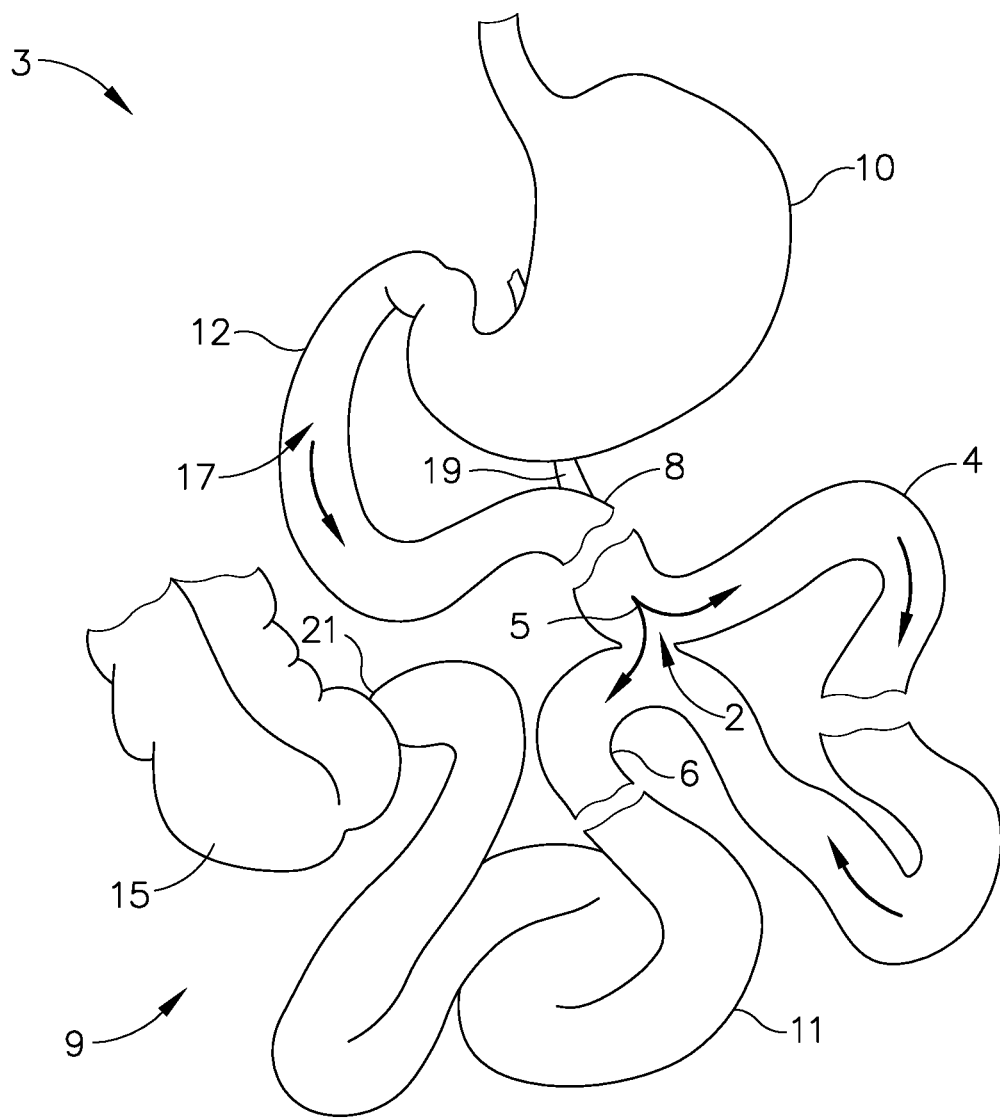
FIG. 1 depicts a diagrammatic view of a portion of a patient's digestive system, showing an anastomosis in the small intestines to divert chyme from the patient's jejunum.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Intestinal Anastomosis

As noted above, it may be desirable to provide an anastomosis between two naturally occurring lumens within a patient's body, such as within the patient's gastrointestinal tract. FIG. 1 shows an example of an anastomosis (2) formed between a proximal portion of a patient's jejunum (4) and the patient's ileum (6). The anastomosis (2) is located just distal to the duodenojujenal flexure (8). The anastomosis (2) provides a path for fluid communication from the proximal portion of a patient's jejunum (4) directly to the ileum (6), thereby providing a bypass of the majority of the jejunum (4). In particular, chyme that exits the stomach (10) may flow directly through the duodenum (12), then through just the proximal portion of the jejunum (4) and directly to the ileum (6) via the anastomosis (2), without passing through the majority of the jejunum (4). In some instances, a portion of the chyme that exits the stomach (10) flows directly from the proximal portion of the jejunum (4) to the ileum (6) via the anastomosis (2); while another portion passes the anastomosis (2) and flows through the remainder of the jejunum (4). Thus, anastomosis (2) may form a complete diversion of chyme or a partial diversion of chyme.

It should be understood that it may be necessary to create at least two enterotomies in order to provide an anastomosis (2)—one opening for the upstream region of the lumen and another opening for the downstream region of the lumen. The tissue surrounding the two enterotomies may be secured together with the enterotomies in alignment in order to provide the anastomosis (2). Once these openings are aligned at the site of the anastomosis (2), a device may be used to compress and hold the tissue together to maintain alignment of the enterotomies forming the anastomosis (2). Holding the tissue together may promote serosa-to-serosa adhesion, such that the serosa that is apposed at the anastomosis (2) eventually bonds together and thereby maintains structural integrity of the anastomosis (2) without the need for assistance by a surgically introduced device. In some instances, it may be necessary to create one or more additional enterotomies in the gastrointestinal tract in order to surgically introduce a device that compresses the tissue together to maintain alignment of the openings forming the anastomosis (2). These additional enterotomies may need to be closed (e.g., using suture, etc.) after the anastomosis compression device has been introduced to the site of the anastomosis (2). The creation and subsequent closure of these additional access enterotomies may impose additional time, cost, and/or risk in the surgical procedure.

The following disclosure includes examples of anastomosis compression devices that may be used to compress and hold the tissue together to maintain alignment and patency of the openings forming the anastomosis (2). It should be understood that each of these devices may be introduced into the lumens of the jejunum and ileum via the same enterotomies that will eventually form the anastomosis (2). In other words, it is not necessary to create (and subsequently close) any additional enterotomies in order to position the below described devices at the site of the anastomosis (2). It should also be understood that the devices described below are configured to maintain their positions at the anastomosis (2) without requiring the devices to be sutured in place. The devices include one device portion that is placed in one part of the gastrointestinal tract and another device portion that is placed in another part of the gastrointestinal tract. These device portions are biased toward each other (e.g., by a resilient member, by magnetic forces, etc.) and thereby compress tissue between opposing surfaces of the device portions. The compression provides a fluid-tight seal at the anastomosis (2), preventing chyme, etc. from leaking at the anastomosis (2). The edges of the opposing device surfaces that contact tissue are rounded or chamfered to prevent the device portions from cutting through the tissue of the gastrointestinal tract. The compressed tissue eventually necroses due to ischemia, such that the device portions and necrosed tissue eventually leave the anastomosis (2) and pass through the gastrointestinal tract.

Figure 2:
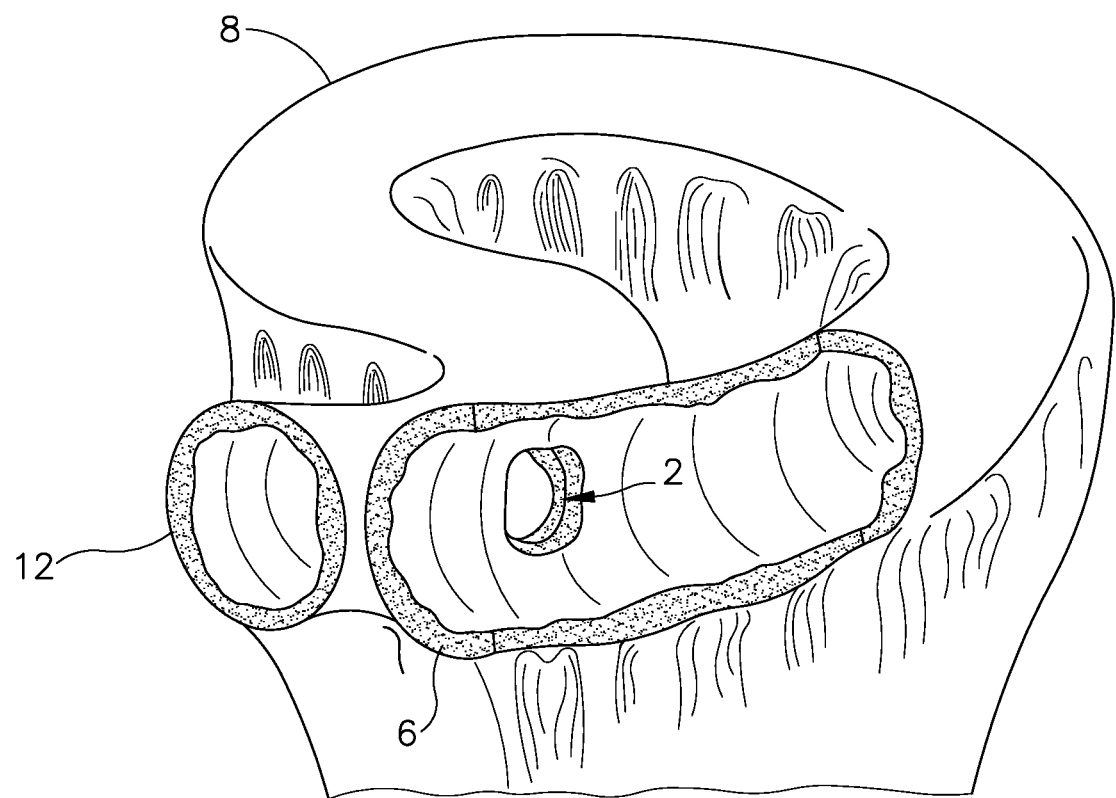
FIG. 2 depicts a partial perspective view of another exemplary anastomosis to divert chyme from the patient's jejunum.

While FIG. 1 shows the anastomosis (2) positioned just distal to the duodenojujenal flexure (8) (e.g., approximately 100 cm distal to the duodenojujenal flexure (8)) and coupling the proximal portion of the jejunum (4) with the ileum (6), it should be understood that an anastomosis (2) may be positioned at various other suitable locations within the gastrointestinal tract. For instance, an anastomosis (2) may be located proximal to the duodenojujenal flexure (8), thus directly coupling the duodenum (12) with the ileum (6) such that chyme may bypass the entire length of the jejunum (4) as shown in FIG. 2. In another example, an anastomosis (2) may be located about 100 centimeters distal to the duodenojujenal flexure (8) and/or ligament of Treitz (19). As another merely illustrative example, an anastomosis (2) may provide a direct coupling between the stomach (10) and jejunum (4), such that chyme may bypass the duodenum (12); or between the esophagus and stomach (10) to reconnect the tract after removing a portion of the esophagus; or between the colon and rectum after removing a portion of the colon due to a lesion, etc. In some examples, the anastomosis (2) may have a side-to-side orientation to connect adjacent portions of a lumen such as the small intestine. Other suitable locations for an anastomosis (2) within the gastrointestinal tract will be apparent to those of ordinary skill in the art in view of the teachings herein. It should also be understood that an anastomosis (2) may be located elsewhere in a patient's body; and that an anastomosis need not necessarily be located within the patient's gastrointestinal tract. It is contemplated that the exemplary anastomosis compression devices described below (and variations thereof) may be used in various locations throughout a patient's body, not just the gastrointestinal tract.

By way of further example, and not limitation, in one example a metabolic pathway of the digestive system (3) is modified by creating a pathway (5) within the intestinal tract (9) by establishing a connection between a proximal location within the small intestine (11) and a distal location within the intestinal tract (9). In the present example, the connection is formed by way of an anastomosis (2). In some examples, the connection is formed by way of a side-to-side anastomosis. Also in the present example, the proximal location within the small intestine (11) is distal to the duodenal papilla (17). In this manner, the pathway (5) serves as a shortcut added to the existing pathway defined by the intestinal tract (9) of the digestive system (3), such that the existing pathway of the intestinal tract (9) remains intact. Accordingly, the procedures involved to create the pathway (5) do not transect, remove, or seal off any portion of the digestive system (3). Furthermore, the procedure is thus fully reversible and the entire digestive system (3) can be fully returned to its original state.

In modifying the metabolic pathway of the digestive system (3) to create the pathway (5), the small intestine (11) itself defines a first initial length. The pathway (5) created defines a second length. This second length is represented as the bypassed region or bypass portion of the intestinal tract (9) that is created due to the anastomosis (2). In this manner, the bypassed region is that length of the intestinal tract (9) that chyme passing through the intestinal tract (9) would not travel through when the chyme instead follows the shortcut pathway created by the anastomosis (2). In this way, the second length can also be defined as the length commencing at the anastomosis (2) at the proximal location in the intestinal tract (9) and terminating at the anastomosis (2) at the distal location in the intestinal tract (9). In the present example the second length can be between about 10% and 70% of the first initial length of the small intestine (11). In one instance of the present example, the second length is less than about 60% of the initial overall length of the small intestine (11).

When performing the method to create the pathway (5) within the intestinal tract (9), natural orifice translumenal endoscopic surgery (also referred to as NOTES) may be used, where the procedure involves one or more flexible endoscopes that are inserted into a patient via a natural orifice of the patient. Such natural orifices can include the mouth or oral cavity for transgastric procedures, the anus for transcolonic procedures, and/or the vagina for transvaginal procedures. Such natural orifices are not limited to only those mentioned above, but may instead include any natural orifice of a patient. In some instances a previous scar site may be used to insert the one or more flexible endoscopes, such as through the navel or umbilicus. In view of the teachings herein, one skilled in the art will recognize that methods for enteroscopy such as double balloon enteroscopy or spiral enteroscopy using a system like the Endo-Ease Discovery® SB made by Spirus Medical, LLC can facilitate the identification of both proximal and distal locations via flexible endoscopy. Furthermore, some procedures for creating the pathway (5) may be performed completely endoscopically, completely laparoscopically, in a completely open procedure, or in a mix of any of these procedure types and/or in combination with natural orifice procedure types. In view of the teachings herein, the various types of procedures and levels of invasiveness that may be used with the methods of creating pathways within the intestinal tract (9) described herein will be apparent to those of ordinary skill in the art.

In the present example, the proximal location, in addition to being distal to the duodenal papilla (17), can be in the duodenum (12), jejunum (4), or the ileum (6). The distal location can be in the jejunum (4), ileum (6), or colon (15). In one instance of the present example, the proximal location is in the duodenum (12), while the distal location is in the jejunum (4). In another instance, the proximal location is in the duodenum (12), while the distal location is in the ileum (6). In another instance, the proximal location is in the jejunum (4), while the distal location is also in the jejunum (4). In another instance, the proximal location is in the jejunum (4), while the distal location is in the ileum (6). In another instance, the proximal location is in the jejunum (4), while the distal location is in the colon (15). In another instance, the proximal location is in the ileum (6), while the distal location is also in the ileum. In another instance, the proximal location is in the ileum (6), while the distal location is in the colon (15). In view of the teachings herein, other locations for the proximal location and the distal location for the created pathway (5) will be apparent to those of ordinary skill in the art.

In the example where the proximal location for the connection is in the jejunum (4) and the distal location is in the colon (15), in one instance the proximal location is at least about 200 centimeters distal from the ligament of Treitz (19). In the example where the proximal location for the connection is in the jejunum (4), in one instance, the proximal location is between about 10 centimeters and about 200 centimeters distal to the ligament of Treitz (19), and in another instance 100 centimeters distal to the ligament of Treitz (19). As mentioned above, in procedures where the proximal location for the connection is in the jejunum (4), one or more flexible endoscopes may be inserted into a patient via the oral cavity and/or the colon (15).

In the example where the distal location for the connection is in the ileum (6), in one instance the distal location is between about 10 centimeters and 300 centimeters proximal to the ileocecal junction (21), and in another instance 250 centimeters proximal to the ileocecal junction (21). In the example where the distal location for the connection is in the colon (15), it may be in either the ascending portion of the colon, the transverse portion of the colon, or the descending portion of the colon. In another example, the distal location is about 250 centimeters proximal to the ileocecal junction (21), while the proximal location is about 100 centimeters from the ligament of Treitz (19).

In an example where the connection is a side-to-side anastomosis (2), the procedure includes forming the anastomosis (2) by compression through an exemplary magnetic anastomosis compression device (100). In such procedures, a first magnetic anastomosis compression device (100) is introduced to a first attachment region at the proximal location and a second magnetic anastomosis compression device (100) is introduced to a second attachment region at the distal location. Also, first magnetic anastomosis compression device (100) includes a contact surface (130) that mates with, or is configured to be oriented adjacent to, a corresponding contact surface (130) on second magnetic anastomosis compression device (100). The procedure further includes compressing a first lumen wall at the first attachment region and a second lumen wall at the second attachment region between first magnetic anastomosis compression device (100) and second magnetic anastomosis compression device (100). Further exemplary features and functionalities that may be incorporated into magnet anastomosis compression device (100) will be described in greater detail below; while others will be apparent to those of ordinary skill in the art in view of the teachings herein. It should be understood, however, that the anastomosis compression devices need not necessarily be used in all versions of the procedures described herein.

In another example where the connection is a side-to-side anastomosis (2), by way of example only and not limitation, the procedure includes forming the anastomosis (2) by mechanical fastening. In this regard the procedure involves creating a first enterotomy at the proximal location, creating a second enterotomy at the distal location, and mechanically fastening the first and second enterotomies (not shown).

By way of further example, and not limitation, in one example the pathway (5) is created within the intestinal tract (9) by forming a first opening (not shown) in a first hollow organ (11), and forming a second opening (not shown) in a second hollow organ (11). It should be understood that the first hollow organ and the second hollow organ can be separate organs or different portions of the same organ. By way of example and not limitation, the first and second hollow organs may be different portions of the small intestine. In other examples the first and second hollow organs may be the small intestine and colon respectively. In view of the teachings herein, other examples for the first and second hollow organs will be apparent to those of ordinary skill in the art.

With the openings created, a first magnetic anastomosis compression device (100) is inserted into one, and a second magnetic anastomosis compression device (100) is inserted into the other. To further create the pathway (5), the first and second hollow organs (11) are moved toward each other to align first magnetic anastomosis compression device (100) and second magnetic anastomosis compression device (100) with each other. With first and second magnetic anastomosis compression devices (100) aligned, their positions are secured relative to each other, and a layer of tissue from each of the first hollow organ (11) and the second hollow organ (11) is compressed in apposition between the secured first and second magnetic anastomosis compression devices (100).

In one instance of the proceeding example for creating the pathway (5) within the intestinal tract (9), the first opening (not shown) is formed within the small intestine (11) at a location distal to the duodenal papilla (17), and the second opening (not shown) is proximal to the ileocecal junction (21). In another instance, the first opening is formed within the small intestine (11) at a location distal to the duodenal papilla (17), and the second opening is distal to the ileocecal junction (21). In yet another instance, the first opening is formed within the jejunum (4) at a location about 100 centimeters (or about one-third the length of the jejunum) distal to the ligament of Treitz (19), and the second opening is formed within the jejunum (4) at a location about 250 centimeters proximal to the ileocecal junction (21). In another instance, the first opening is formed in a proximal portion of the jejunum (4), and the second opening is formed distal to the first opening (70) at a distance between about 10% and about 70% of the length of the small intestine (11).

The above examples and procedures are merely exemplary and various modifications in the locations used or steps performed in creating one or more pathways within the digestive system of a patient will be apparent to those or ordinary skill in the art in view of the teachings herein.

The procedures described above and elsewhere herein may be performed using any of the various devices described below. In addition, or in the alternative, the procedures described above and elsewhere herein may be performed using any of the devices described in U.S. Pat. No. 8,828,031, entitled "Apparatus for Forming an Anastomosis," issued Sep. 9, 2014, the disclosure of which is incorporated by reference herein; U.S. Pat. No. 8,828,032, entitled "Methods and Apparatus for Magnet-Induced Compression Anastomosis Between Adjacent Organs," issued Sep. 9, 2014, the disclosure of which is incorporated by reference herein; U.S. Pat. No. 7,445,622, entitled "Anastomotic Ring Applier with Double Motion Actuation," issued Nov. 4, 2008, the disclosure of which is incorporated by reference herein; U.S. Pat. No. 8,142,454, entitled "Apparatus and Method for Magnetic Alteration of Anatomical Features," issued Mar. 27, 2012, the disclosure of which is incorporated by reference herein; U.S. Pat. No. 6,171,320, entitled "Surgical Clip," issued Jan. 9, 2001, the disclosure of which is incorporated by reference herein; U.S. Pat. No. 8,870,899, entitled "Self-Assembling Magnetic Anastomosis Device Having an Exoskeleton," issued Oct. 28, 2014, the disclosure of which is incorporated by reference herein; U.S. Pat. No. 7,780,686, entitled "Anastomotic Device," issued Aug. 24, 2010, the disclosure of which is incorporated by reference herein; U.S. Pat. No. 7,637,919, entitled "Anastomosis System for Performing Anastomosis in Body," issued Dec. 29, 2009, the disclosure of which is incorporated by reference herein; U.S. Pat. No. 8,197,498, entitled "Gastric Bypass Devices and Procedures," issued Jun. 12, 2012, the disclosure of which is incorporated by reference herein; U.S. Pat. No. 9,381,041, entitled "Methods and Devices for Access Across Adjacent Tissue Layers," issued Jul. 5, 2016, the disclosure of which is incorporated by reference herein; U.S. Pat. No. 8,864,781, entitled "Intestinal Bypass Using Magnets," issued Oct. 21, 2014, the disclosure of which is incorporated by reference herein; U.S. Pat. No. 8,684,995, entitled "Treatment Method," issued Apr. 1, 2014, the disclosure of which is incorporated by reference herein; U.S. Pat. No. 9,456,820, entitled "Incisionless Gastric Bypass Method and Devices," issued Oct. 4, 2016, the disclosure of which is incorporated by reference herein; U.S. Pub. No. 2011/0137394, entitled "Methods and Systems for Penetrating Adjacent Tissue Layers," published Jun. 9, 2011, now abandoned, the disclosure of which is incorporated by reference herein; U.S. Pub. No. 2007/0142850, entitled "Compression Anastomosis Device," published Jun. 21, 2007, now abandoned, the disclosure of which is incorporated by reference herein; U.S. Pub. No. 2006/0036267, entitled "Methods and Apparatus for Performing Malabsorptive Bypass Procedures within a Patient's Gastro-Intestinal Lumen," published Feb. 16, 2006, now abandoned, the disclosure of which is incorporated by reference herein; U.S. Provisional Patent App. No. 61/697,845, entitled "Magnetic Compression Anastomosis Device," filed Sep. 7, 2012, the disclosure of which is incorporated by reference herein; U.S. Pat. No. 9,364,238, entitled "Method and Apparatus for Joining Hollow Organ Sections in Anastomosis," issued Jun. 14, 2016, the disclosure of which is incorporated by reference herein; U.S. patent application Ser. No. 15/298,816, entitled "Method for Partial Diversion of the Intestinal Tract," filed Oct. 20, 2016, published as U.S. Pub. No. 2017/0035425 on Feb. 9, 2017, the disclosure of which is incorporated by reference herein; the journal article entitled "Endoscopic Intestinal Bypass Creation by Using Self-Assembling Magnets in a Porcine Model," by Dr. Marvin Ryou et al., from Gastrointestinal Endoscopy, Vol. 83, No. 4, pp. 821-25, 2016, and/or the journal article entitled "Minimally Invasive Entero-Enteral Dual-Path Bypass Using Self-Assembling Magnets," by Dr. Marvin Ryou et al., from Surgical Endoscopy, published online by Springer Feb. 19, 2016. Still other devices that may be used to perform the procedures described herein will be apparent to those of ordinary skill in the art in view of the teachings herein.

II. Exemplary Magnetic Compression Device with Degradable Retention Feature

In some instances, it may be beneficial for an anastomosis device to be able to be installed in a wide, expanded state; then eventually transition to a narrow, contracted state. The wide, expanded state may be beneficial upon installation of the anastomosis device in the patient, as the wide, expanded state may maximize patency through an anastomosis that is secured by the anastomosis device. However, after the anastomosis is completely formed and the anastomosis device is freed from the anastomosis site, it may be beneficial for the anastomosis device to collapse to a narrow, contracted state in order to promote passage of the anastomosis site through the remainder of the patient's digestive tract.

The following description provides various examples of anastomosis devices that are configured to transition from a wide, expanded state to a narrow, contracted state after the anastomosis devices have been installed in a patient. In particular, the following examples include a resilient feature that is configured to resiliently bias the anastomosis device toward a narrow, contracted state; and a degradable feature that is configured to temporarily maintain the anastomosis device in a wide, expanded state. It should be understood that the anastomosis devices described below may be used in any of the various anastomosis procedures described above and in any of the various anastomosis procedures described in the various references described herein. Other suitable ways in which the below-described anastomosis devices may be used will be apparent to those of ordinary skill in the art in view of the teachings herein.

A. Exemplary Magnetic Compression Device with Degradable Resilient Band

Figure 3A:
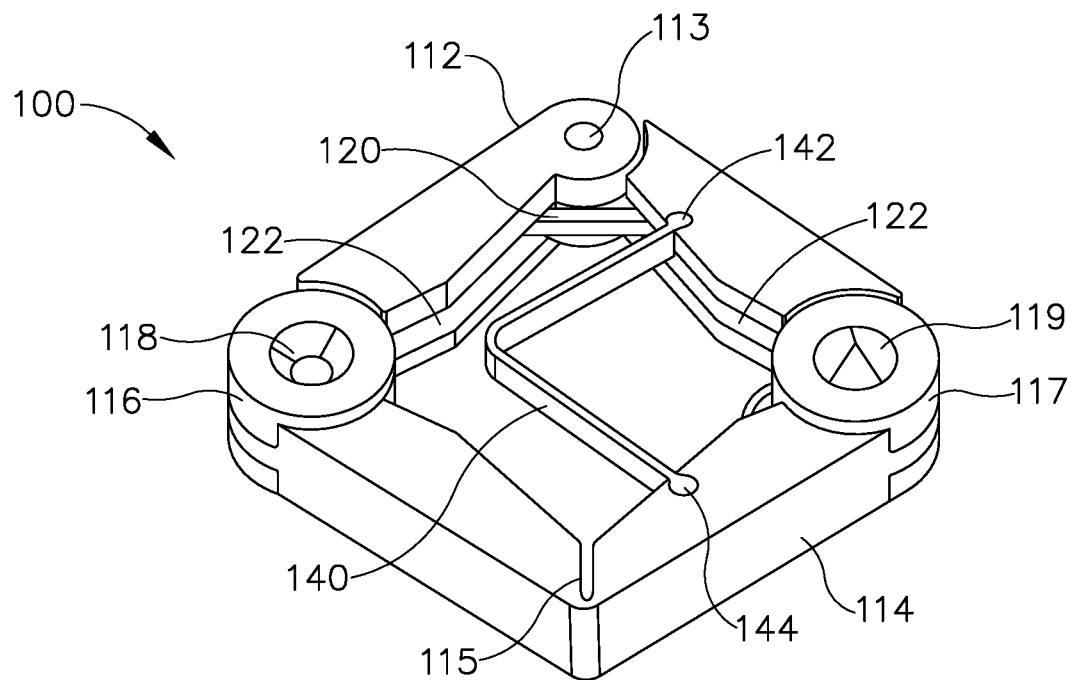
FIG. 3A depicts a perspective view of an exemplary magnetic anastomosis compression device, in a wide configuration.

FIG. 3A shows an exemplary magnetic anastomosis compression device (100) comprising a first collapsible arm (112) and a second collapsible arm (114). First collapsible arm (112) and second collapsible arm (114) are pivotably connected at a first joint (116) and at a second joint (117). First collapsible arm (112) and second collapsible arm (114) are configured to transition between a wide, expanded state (see FIG. 3A) and a narrow, collapsed state (see FIG. 3B) about joints (116, 117). First joint (116) further comprises a magnet (118) that is sized and shaped to have a concave configuration, recessed within first joint (116). Similarly, second joint (117) further comprises a magnet (119) that is sized and shaped to have a convex configuration, protruding from second joint (117). The protruding shape of magnet (119) is configured to mate with the corresponding recessed shape of magnet (118). Magnets (118, 119) are oriented such that concave magnet (118) presents a first magnetic pole (e.g., north) and convex magnet (119) presents a second magnetic pole (e.g., south).

Figure 3B:
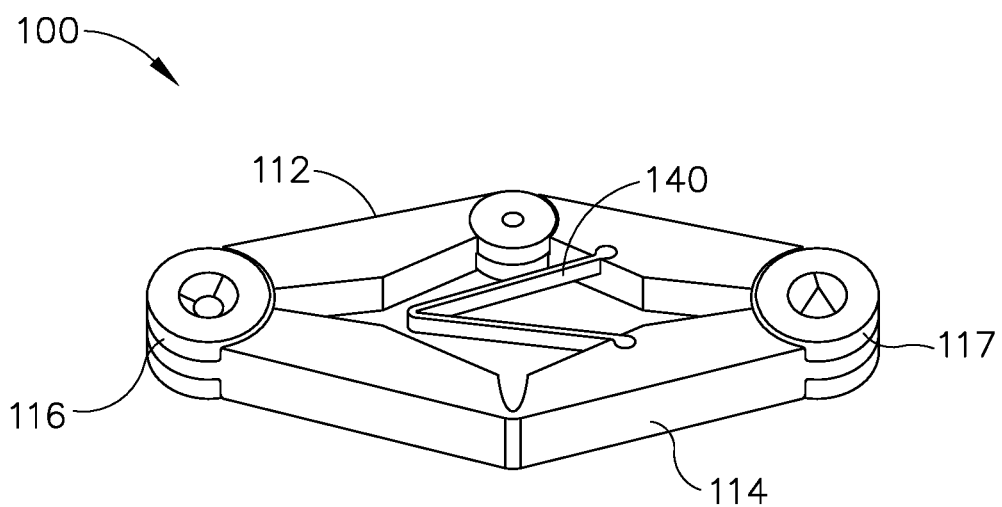
FIG. 3B depicts a perspective view of the anastomosis compression device of FIG. 3A, in a narrow configuration.

Magnetic anastomosis compression device (100) further comprises a mid-joint (113) positioned along first collapsible arm (112) between first joint (116) and second joint (117), such that mid-joint (113) provides a pivotal connection between segments of first collapsible arm (112). Second collapsible arm (114) comprises a living hinge (115) positioned between first joint (116) and second joint (117), such that living hinge (115) provides a pivotal connection between segments of second collapsible arm (114). Mid-joint (113) of first collapsible arm (112) and living hinge (115) of second collapsible arm (114) are configured to allow for the collapsing movement of first collapsible arm (112) and second collapsible arm (114) when flexibly changing configurations about joints (116, 117) from a wide configuration (see FIG. 3A) to a narrow configuration as seen in FIG. 3B. Although not shown, it should be understood that mid-joint (113) may be positioned along second collapsible arm (114). Similarly, living hinge (115) may be positioned on first collapsible arm (112). As will be apparent to those of ordinary skill in the art in view of the teachings herein, magnetic anastomosis compression device (100) may include multiple mid-joints (113) or living hinges (115).

Magnetic anastomosis compression device (100) further comprises a degradable resilient band (120) positioned adjacent mid-joint (113) of first collapsible arm (112). Resilient band (120) attaches to each segment of first collapsible arm (112), within an elongate slot (122). Elongate slot (122) is positioned along the longitudinal length of first collapsible arm (112) and is sized to receive resilient band (120). Resilient band (120) provides a resilient bias urging compression device (100) toward the wide, expanded configuration shown in FIG. 3A. Although not shown, it should be understood that multiple resilient bands (120) may be included within elongate slot (122) of first collapsible arm (112). As will also be apparent to those of ordinary skill in the art in view of the teachings herein, resilient band (120) and elongate slot (122) may be positioned along second collapsible arm (114) of magnetic anastomosis compression device (100).

Additionally, magnetic anastomosis compression device (100) comprises a spring member (140) positioned between first collapsible arm (112) and second collapsible arm (114). Spring member (140) attaches to first collapsible arm (112) at a junction point (142) and to second collapsible arm (114) at a junction point (144). Spring member (140) is configured to resiliently bias first collapsible arm (112) and second collapsible arm (114) inwardly toward each other. In other words, spring member (140) is resiliently biased to urge compression device (100) toward the narrow, collapsed configuration shown in FIG. 3B.

In the present example, the biasing force exerted by resilient band (120) is greater than the biasing force exerted by spring member (140), such that magnetic anastomosis compression device (100) remains in a wide configuration until the bias of resilient band (120) is removed.

In the present example, resilient band (120) is formed of a degradable material. Various suitable materials that may be used to form resilient band (120) will be apparent to those of ordinary skill in the art in view of the teachings herein. In particular, resilient band (120) is configured to degrade after a predetermined amount of exposure to the gastrointestinal tract of a patient's body. First collapsible arm (112), second collapsible arm (114), and spring member (140) are each formed of a nondegradable material. While resilient band (120) is fully intact, magnetic compression device (100) remains in a wide configuration, as seen in FIG. 3A. Upon the degradation of resilient band (120), the biasing force provided by resilient band (120) is removed and the biasing force exerted by spring member (140) overtakes. At this point, spring member (140) causes first collapsible arm (112) and second collapsible arm (114) to collapse inwardly towards each other, causing magnetic anastomosis compression device (100) to transition to the narrow configuration as seen in FIG. 3B.

Alternatively, although not shown, it should be understood that spring member (140) may comprise a degradable composition. As will be apparent to those of ordinary skill in the art in view of the teachings herein, spring member (140) may be configured to bias first collapsible arm (112) and second collapsible arm (114) outwardly from each other. In this alternative version, magnetic anastomosis compression device (100) does not include a resilient band (120) along first collapsible arm (112). Instead, upon the degradation of spring member (140), the outward biasing force exerted by spring member (140) is removed thus allowing first collapsible arm (112) and second collapsible arm (114) to move freely about joints (116, 117) between a wide configuration (see FIG. 3A) and a narrow configuration as seen in FIG. 3B. Thus, the inner walls of the patient's gastrointestinal tract may cause such versions of compression device (100) to transition to the narrow, collapsed state.

Figure 4A:
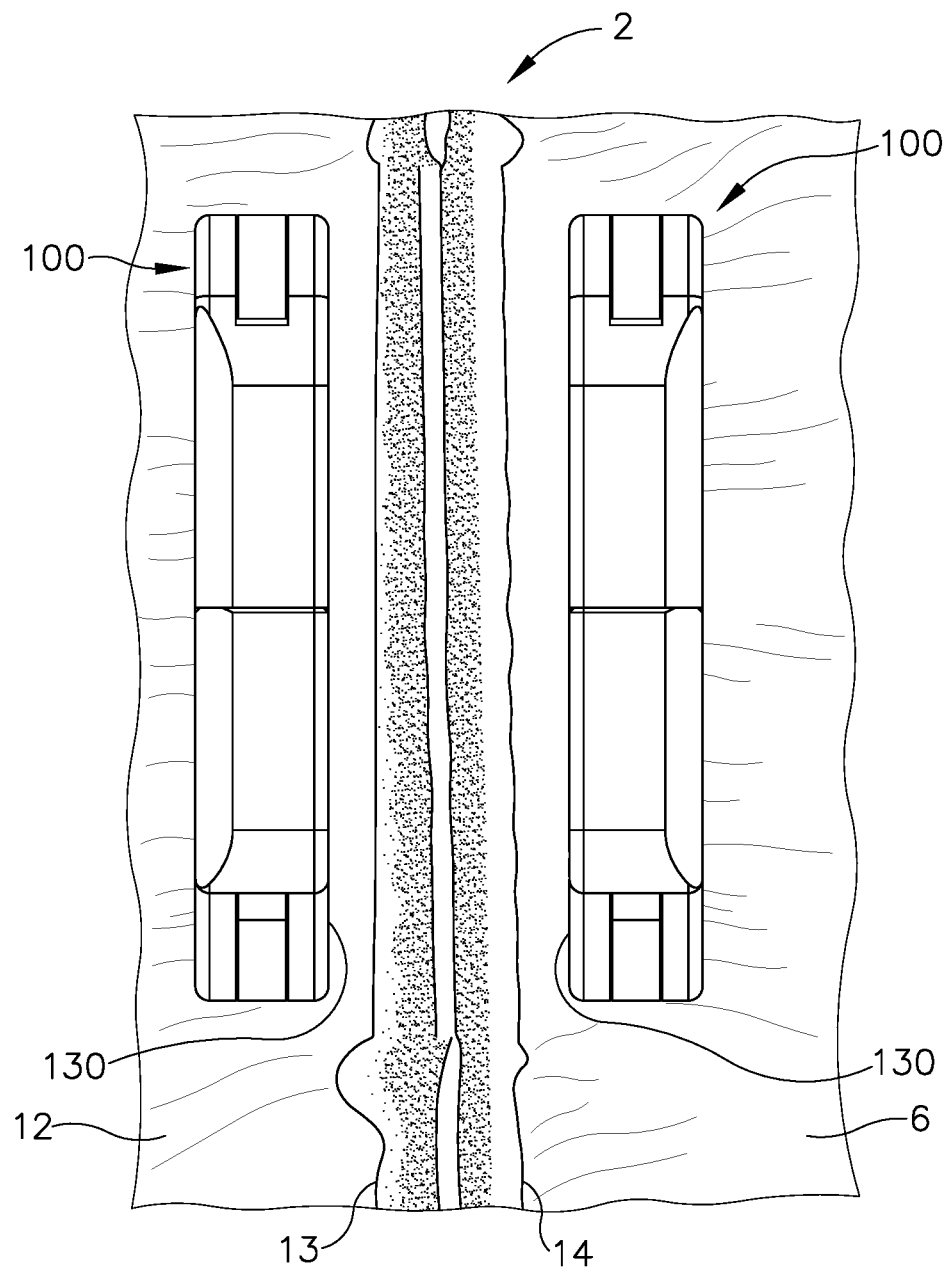
FIG. 4A depicts a cross-sectional view of a pair of the anastomosis compression devices of FIG. 3A, oppposingly positioned in different regions of a patient's small intestine, with live tissue positioned between opposing surfaces of the anastomosis compression devices.
Figure 4B:
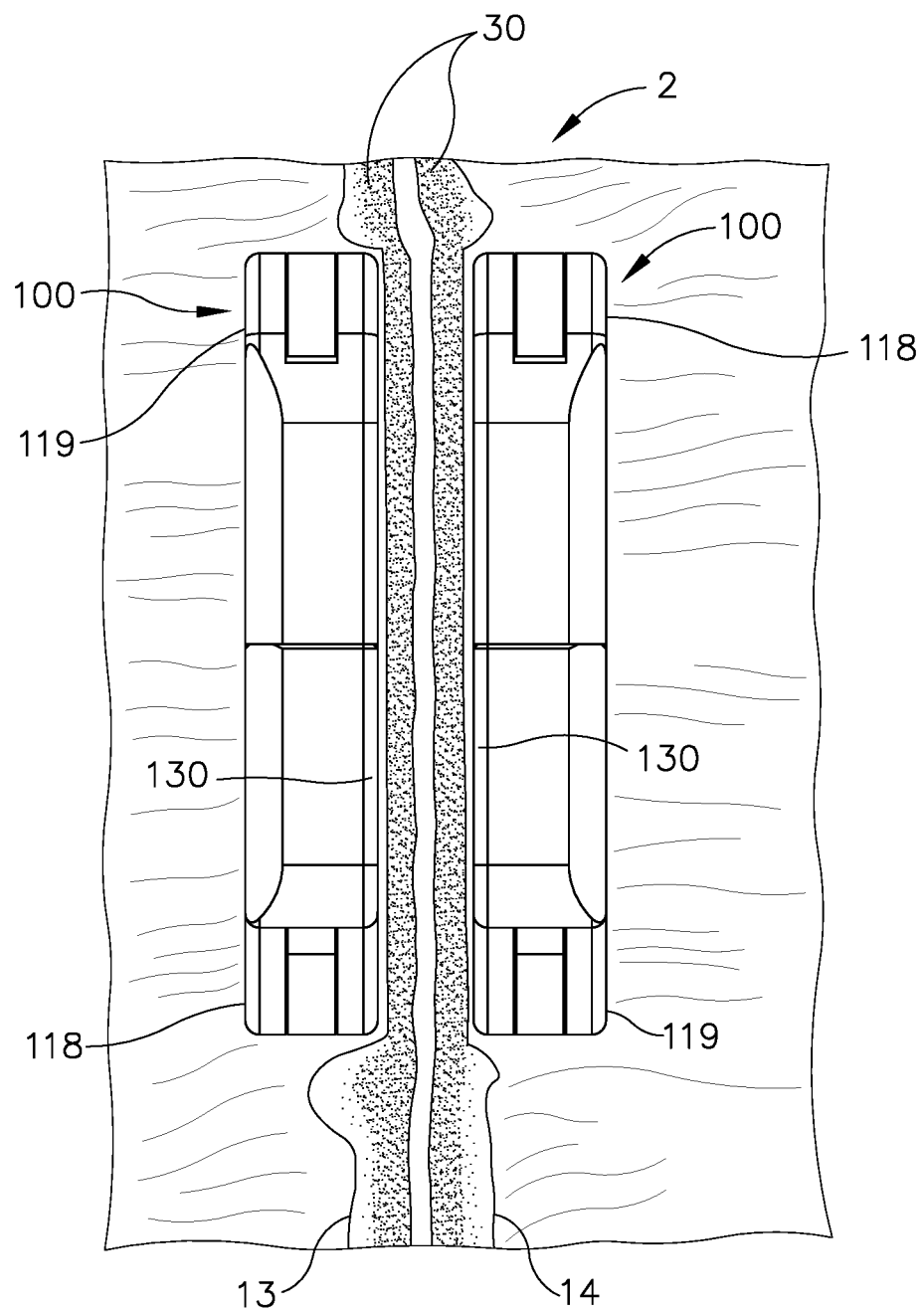
FIG. 4B depicts a cross-sectional view of a pair of the anastomosis compression devices of FIG. 4A, magnetically drawn to each other in a patient's small intestine, with the tissue positioned between the opposing surfaces of the magnetic anastomosis compression devices in a state of necrosis.
Figure 4C:
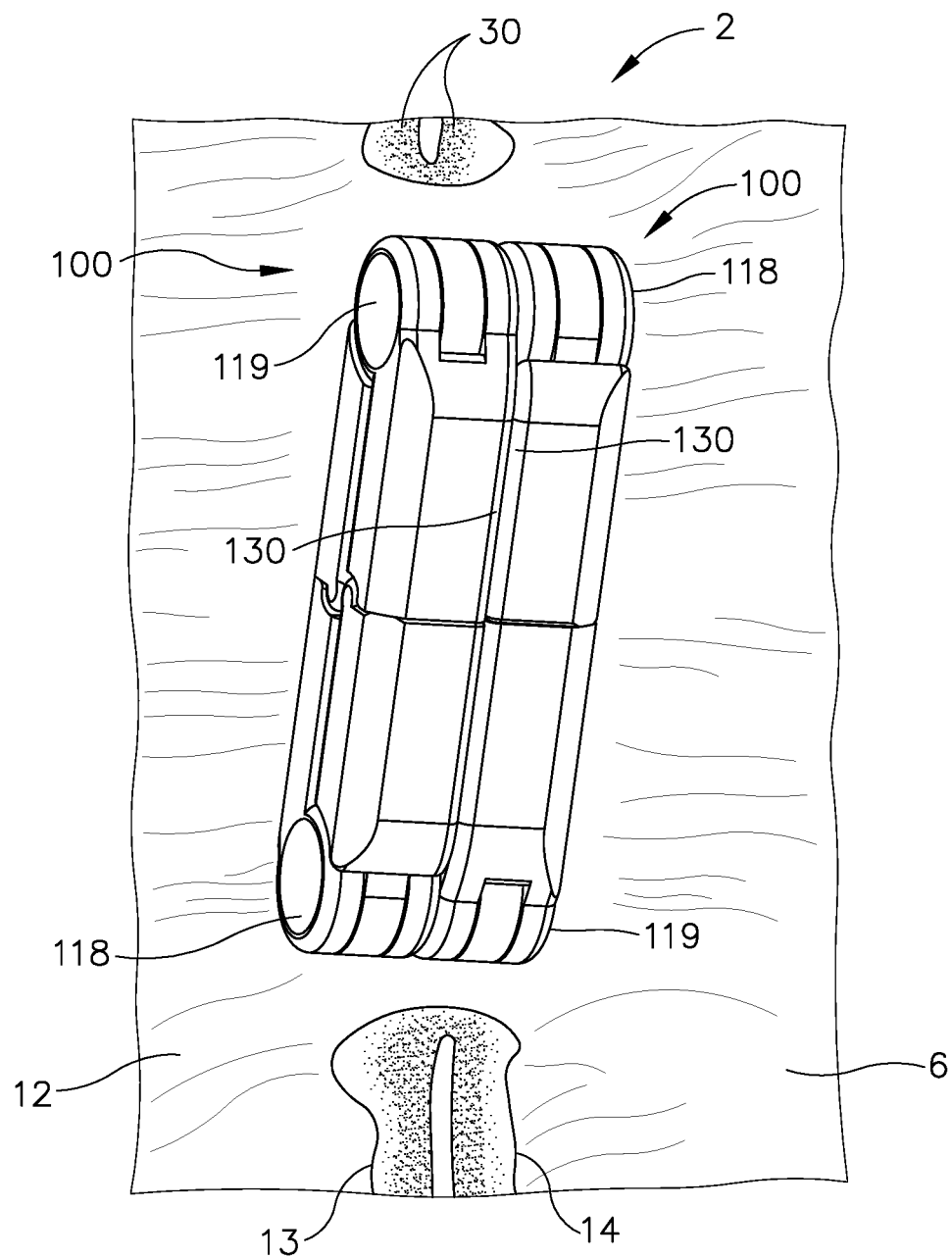
FIG. 4C depicts a cross-sectional view of a pair of the anastomosis compression devices of FIG. 4A, with the magnetic compression devices magnetically fixed to each other, with biasing elements of the anastomosis compression devices degraded, with the anastomosis compression devices each in a narrow configuration, with the anastomosis compression devices beginning to leave the anastomosis and pass through the patient's small intestine while leaving behind a secure anastomosis.

FIGS. 4A-4C show an exemplary procedure in which a pair of compression devices (100) are used. In particular, in a side-to-side anastomosis (2), the procedure includes forming an anastomosis (2) by compression through the use of two compression devices (100). It should be understood that, at the beginning stage shown in FIG. 4A, compression devices (100) are each in the wide, expanded configuration of FIG. 3A. It should also be understood that, while each compression device (100) is en route to the anastomosis site, each compression device (100) may be held in the narrow, contracted configuration shown in FIG. 3B. This may facilitate transport of compression devices (100) in a deployment instrument, through a deployment port, and/or through an enterotomy. Once each compression device (100) reaches its respective position at or near the anastomosis site, each compression device (100) may be allowed to expand to the wide, expanded configuration of FIG. 3A (e.g., as biased by resilient band (120)).

Referring to FIG. 4A, in such procedures a first magnetic anastomosis compression device (100) is introduced into a first region of a patient's gastrointestinal tract (for exemplary purposes, an ileum (6)) through an enterotomy (not shown). Simultaneously, a second magnetic anastomosis compression device (100) is introduced into another region of a patient's gastrointestinal tract (for exemplary purposes, a duodenum (12)) through a separate enterotomy (not shown). Both magnetic anastomosis compression devices (100) include a contact surface (130) that mates with, or is configured to be oriented against, the corresponding contact surface (130) of the other magnetic anastomosis compression device (100).

The procedure further includes moving the two magnetic anastomosis compression devices (100) toward each other. Once aligned with one another, an operator may press a first one of the compression devices (100) against a first lumen wall (13) at the first attachment region where the first one of the magnetic compression devices (100) is positioned; and press a second one of the compression devices (100) against a second lumen wall (14) at the second attachment region where the second magnetic compression device (100) is located.

As best seen in FIG. 4B, between contact surfaces (130) of the exemplary magnetic compressions devices (100) is a layer of tissue (30) from each of the first lumen wall (13) and the second lumen wall (14). It should be understood that, at this stage, a concave magnet (118) of the first compression device (100) would be aligned with a convex magnet (119) of the second compression device (100); and a convex magnet (119) of the first compression device (100) would be aligned with a concave magnet (118) of the second compression device (100). The complementary, nesting configurations of magnets (118, 119) may promote alignment of the first compression device (100) with the second compression device (100). In addition, or in the alternative, the complementary, nesting configurations of magnets (118, 119) may provide some degree of deformation in the tissue (30) of walls (13, 14), which may further secure the positioning of compression devices (100) along walls (13, 14). It should also be understood that the magnetic fields of magnets (118, 119) may pass through walls (13, 14), such that the opposing magnetic poles provided by magnets (118, 119) may provide magnetic attraction between the two compression devices (100). This magnetic attraction may further secure the positioning of compression devices (100) and provide enhanced compression of the tissue (30) apposed between compression devices (100).

As magnets (118, 119) are pulled closer together by their magnetic charge, tissue (30) of lumen walls (13, 14) are compressed further between the respective contacting surfaces (130) of the magnetic compression devices (100), as seen in FIG. 4B. At this point, resilient band (120) continues to maintain its structure and composition while remaining fully intact despite its initial exposure to the gastrointestinal tract of the patient's body.

Over time, the ischemia caused by the compression of magnetic anastomosis compression devices (100) against tissue (30) eventually results in necrosis of the tissue (30), as shown in FIG. 4C. This necrosis eventually reaches a point where lumen walls (13, 14) can no longer structurally support magnetic anastomosis compression devices (100), such that compression devices (100) break free from the site of the anastomosis (2). Magnetic compression devices (100) remain held together though the engagement of magnets (118, 119) of each respective magnetic compression device (100) such that contact surfaces (130) are securely pressed against each other.

Since magnetic anastomosis compression devices (100) have now been exposed to the gastrointestinal tract of the patient's body for an amount of time in excess of the predetermined amount tolerable by resilient bands (120), resilient bands (120) of each magnetic anastomosis compression device (100) have degraded and are no longer fixed at their original positions along first collapsible arm (112). Due to this, magnetic anastomosis compression devices (100) are no longer constrained in their wide configurations (see FIG. 3A), thus allowing spring members (140) to force first arms (112) and second arms (114) of magnetic anastomosis compression devices (100) to collapse towards each other into a narrow configuration, as seen in FIG. 4C. It should be understood that resilient bands (120) may degrade, to the point where resilient bands (120) no longer counteract spring members (140), at any suitable time between the stage shown in FIG. 4B and the stage shown in FIG. 4C. However, in the present example, resilient bands (120) have both degraded to the point where resilient bands (120) no longer counteract spring members (140) by the time the process reaches the stage shown in FIG. 4C.

As seen in FIG. 4C, magnetic compression devices (100) remain held together due to the engagement of magnets (118, 119). Now in their narrow configuration, magnetic anastomosis compression devices (100) will pass into the ileum (6) and eventually pass into the bowels and out from the patient with feces. When magnetic anastomosis compression devices (100) leave the site of the anastomosis (2), the structural integrity of the anastomosis (2) remains secure due to natural tissue adhesions. In particular, the exterior of the duodenum (12) and the ileum (6) may have substantial serosa-to-serosa adhesion at this point, due to the sustained contact between the duodenum (12) and the ileum (6). In addition, the mucosa at the interior of the duodenum (12) and the ileum (6) may have remodeled itself to provide a smooth mocuosal transition (90) between the duodenum (12) and the ileum (6) at the site of the anastomosis (2), as shown in FIG. 4C. With the anastomosis (2) complete, chyme may freely pass from the duodenum (12) to the ileum (6) via the anastomosis (2), without needing to pass through the jejunum (4).

B. Exemplary Magnetic Compression Device with Degradable Resilient Suture

Figure 5A:
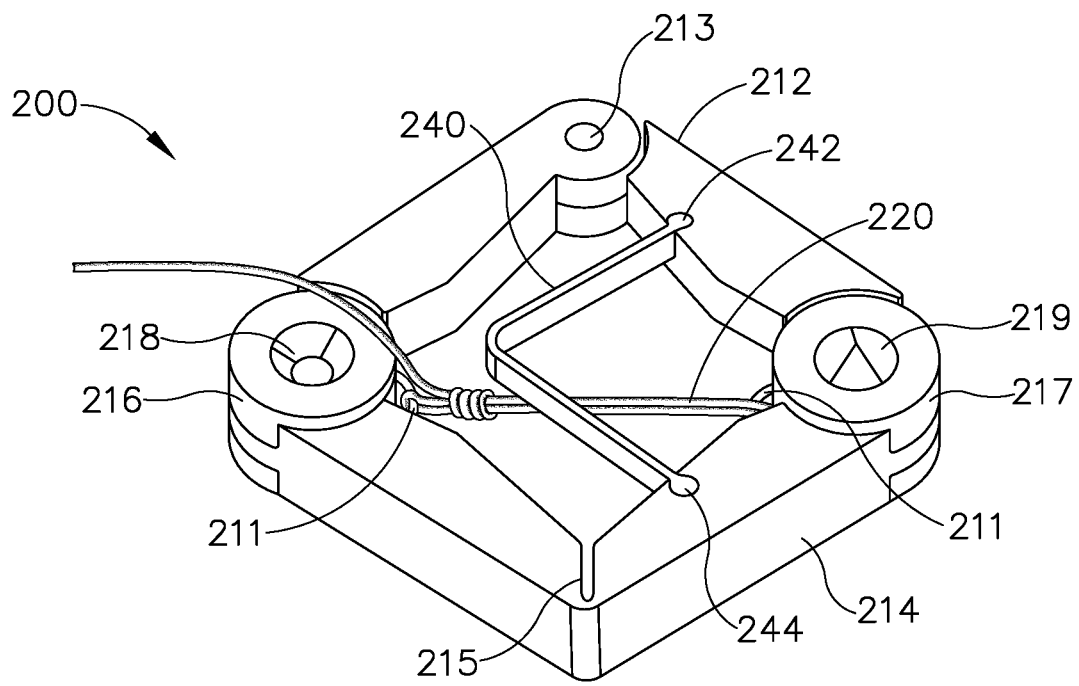
FIG. 5A depicts a perspective view of an exemplary alternative anastomosis compression device, in a wide configuration.

FIG. 5A shows an exemplary alternative magnetic anastomosis compression device (200). Magnetic anastomosis compression device (200), similar to magnetic compression device (100), comprises a first collapsible arm (212) and a second collapsible arm (214). Collapsible arms (212, 214) are pivotably connected at a first joint (216) and at a second joint (217). First collapsible arm (212) and second collapsible arm (214) are configured to transition between a wide, expanded state (see FIG. 5A) and a narrow, collapsed state (see FIG. 5B) about joints (216, 217). First joint (216) further comprises a magnet (218) that is sized and shaped to have a concave configuration, recessed within first joint (216). Similarly, second joint (217) further comprises a magnet (219) that is sized and shaped to have a convex configuration, protruding from second joint (217). The protruding shape of magnet (219) is configured to mate with the corresponding recessed shape of magnet (218). Magnets (218, 219) are oriented such that concave magnet (218) presents a first magnetic pole (e.g., north) and convex magnet (219) presents a second magnetic pole (e.g., south).

Figure 5B:
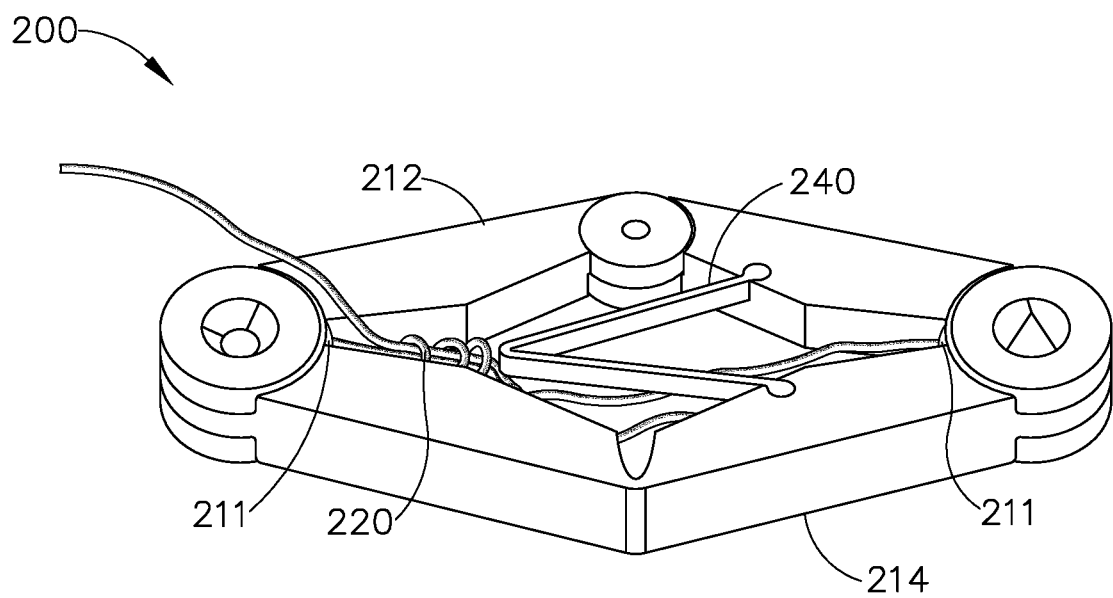
FIG. 5B depicts a perspective view of the anastomosis compression device of FIG. 5A, in a narrow configuration.

Magnetic anastomosis compression device (200) further comprises a mid-joint (213) positioned along first collapsible arm (212) between first joint (216) and second joint (217), such that mid-joint (213) provides a pivotal connection between segments of first collapsible arm (212). Second collapsible arm (214) comprises a living hinge (215) positioned between first joint (216) and second joint (217), such that living hinge (215) provides a pivotal connection between segments of second collapsible arm (214). Mid-joint (213) of first collapsible arm (212) and living hinge (215) of second collapsible arm (214) are configured to allow for the collapsing movement of first collapsible arm (212) and second collapsible arm (214) when flexibly changing configurations about joints (216, 217) from a wide configuration (see FIG. 5A) to a narrow configuration as seen in FIG. 5B. Although not shown, it should be understood that mid-joint (213) may be positioned along second collapsible arm (214). Similarly, living hinge (215) may be positioned on first collapsible arm (212). As will be apparent to those of ordinary skill in the art in view of the teachings herein, magnetic anastomosis compression device (200) may include multiple mid-joints (213) or living hinges (215).

In the present example, magnetic anastomosis compression device (200) further comprises a degradable resilient suture (220) positioned between first joint (216) and second joint (217). Resilient suture (220) is formed of a resilient and degradable material in the present example. Various suitable kinds of materials that may be used to form resilient suture (220) will be apparent to those of ordinary skill in the art in view of the teachings herein. Resilient suture (220) attaches to joints (216, 217) by tying around rings (211), though any other suitable components and techniques may be used to secure resilient suture (220) to joints (216, 217).

In the present example, resilient suture (220) produces a resilient bias urging compression device (200) toward the wide, expanded configuration shown in FIG. 5A. In some other versions, suture (220) is not resilient and simply provides tension to hold compression device (200) in the wide, expanded configuration shown in FIG. 5A until suture (220) degrades as described below. Although not shown, it should be understood that multiple resilient sutures (220) and rings (211) may be included between first collapsible arm (212) and second collapsible arm (214). As will also be apparent to those of ordinary skill in the art in view of the teachings herein, resilient suture (220) may be configured along varying positions on magnetic anastomosis compression device (200).

Additionally, magnetic compression device (200) comprises a spring member (240) positioned between first collapsible arm (212) and second collapsible arm (214). Spring member (240) attaches to first collapsible arm (212) at a junction point (242) and to second collapsible arm (214) at a junction point (244). Spring member (240) is configured to resiliently bias first collapsible arm (212) and second collapsible arm (214) inwardly toward each other. In other words, spring member (240) is resiliently biased to urge compression device (200) toward the narrow, collapsed configuration shown in FIG. 5B.

In the present example, the biasing force exerted by resilient suture (220) is greater than the biasing force exerted by spring member (240), such that magnetic anastomosis compression device (200) remains in a wide configuration until the bias of resilient suture (220) is removed.

As noted above, resilient suture (220) of the present example is formed of a degradable material such that resilient suture (220) is configured to degrade after a predetermined amount of exposure to the gastrointestinal tract of a patient's body. First collapsible arm (212), second collapsible arm (214), and spring member (240) are each formed of a nondegradable material. While resilient suture (220) is fully intact, magnetic compression device (200) remains in a wide configuration, as seen in FIG. 5A. Upon the degradation of resilient suture (220), the biasing force created by resilient suture (220) is removed and the biasing force exerted by spring member (240) overtakes. The biasing force exerted by spring member (240) thereby causes first collapsible arm (212) and second collapsible arm (214) to collapse inwardly toward each other, causing magnetic compression device (200) to transition to the narrow configuration, as seen in FIG. 5B.

The procedure of forming an anastomosis (2) by compression of two exemplary magnetic anastomosis compression devices (200) is identical to the procedure depicted in FIGS. 4A-4C for magnetic anastomosis compression device (100). It should also be understood that, while each compression device (200) is en route to the anastomosis site, each compression device (200) may be held in the narrow, contracted configuration shown in FIG. 5B. This may facilitate transport of compression devices (200) in a deployment instrument, through a deployment port, and/or through an enterotomy. Once each compression device (200) reaches its respective position at or near the anastomosis site, each compression device (200) may be allowed to expand to the wide, expanded configuration of FIG. 5A (e.g., as biased by resilient suture (220)). In variations where suture (220) is non-resilient, the operator may hold compression device (200) in the expanded configuration of FIG. 5A, draw suture (220) to provide tension in suture (220), then secure (e.g., knot, clip, etc.) suture (220) in order to maintain the tension in suture (220) until suture (220) degrades.

After compression devices (200) are placed in the gastrointestinal tract of the patient, resilient suture (220), similar to resilient band (120) of magnetic compression device (100), ultimately experiences degradation in response to fluids and/or temperature conditions within the gastrointestinal tract of the patient's body for an amount of time in excess of the predetermined amount tolerable by resilient suture (220). The degradation of resilient sutures (220) of each magnetic compression device (200) causes the portion of resilient suture (220) tied around rings (211) to unravel. At this point, the biasing force exerted by resilient suture (220) against the opposing-biasing force of spring member (240) is removed. Due to this, magnetic anastomosis compression device (200) is no longer constrained to the wide configuration (see FIG. 5A), thus allowing the biasing force of spring member (240) to overtake and force first collapsible arms (212) and second collapsible arms (214) of both magnetic anastomosis compression devices (200) to collapse toward each other to a narrow configuration, as seen in FIG. 5B. As noted above with respect to magnetic compression devices (100), magnetic compression devices (200) may thereby more easily pass through the remainder of the patient's gastrointestinal tract after detaching from the anastomosis site.

While the foregoing example describes suture (220) as being degradable, it should be understood that, in some versions, only a portion of suture (220) is degradable. For instance, suture (220) may include one or more degradable regions adjacent to one or more non-degradable regions. As another merely illustrative variation, suture (220) may be formed of a non-degradable material; while a degradable component temporarily secures tension in suture (220). For instance, a non-degradable suture (220) may be placed in tension (e.g., by shortening the effective length of suture (220) while compression device (200) is held in the wide, expanded configuration of FIG. 5A), and a degradable clip may be applied to suture (220) in order to maintain the tension until the clip degrades.

Figure 6:
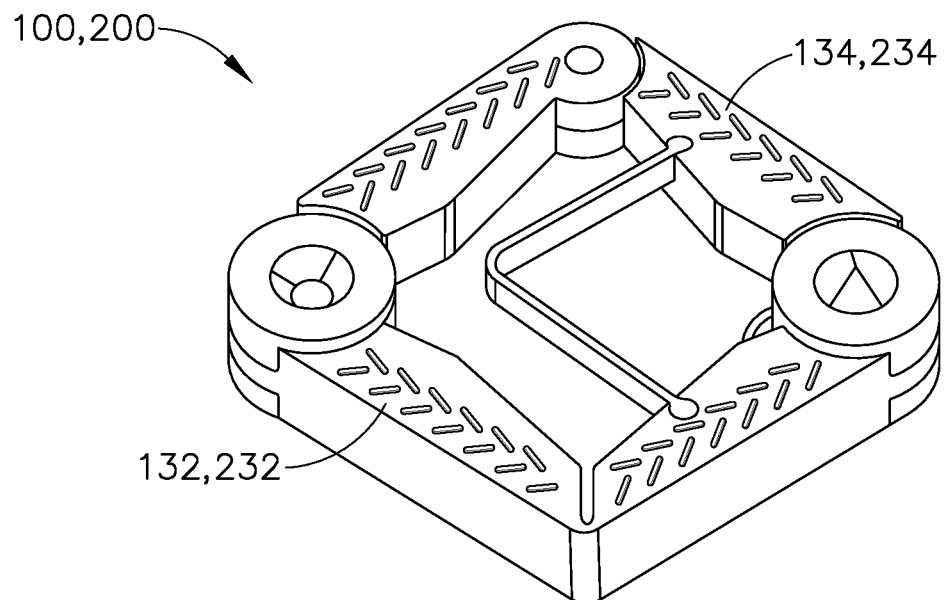
FIG. 6 depicts a perspective view of an exemplary variation of the anastomosis compression devices of FIGS. 4A and 5A, with tissue gripping features on the surface of the device, and with the anastomosis compression device in a wide configuration.
Figure 7:
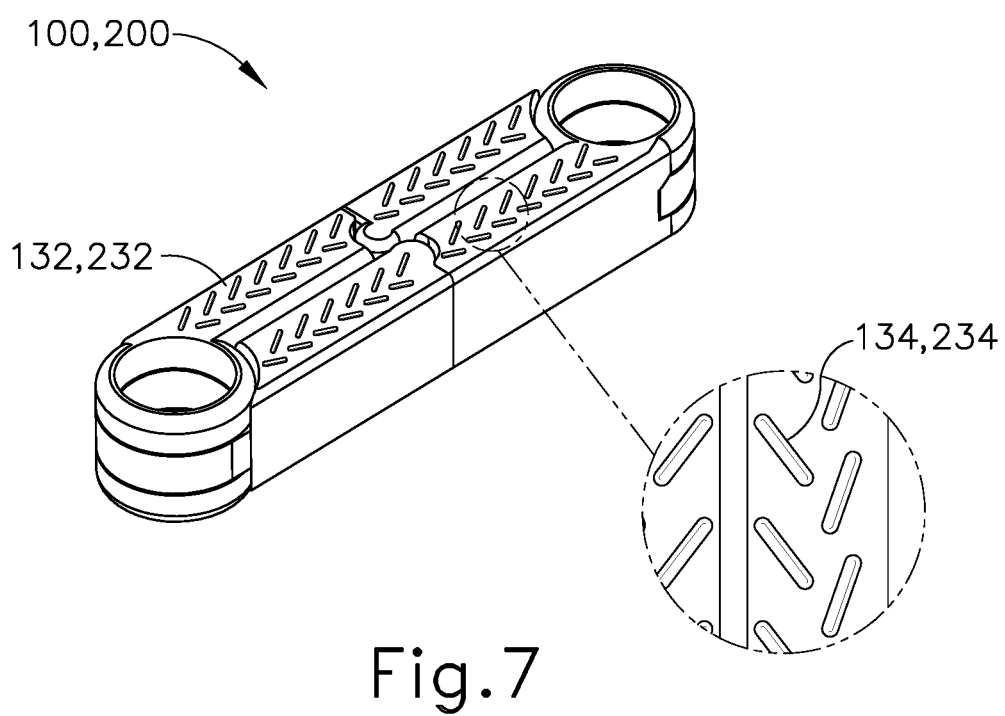
FIG. 7 depicts a cross sectional view of the anastomosis compression device of FIG. 6, with the anastomosis compression device in a narrow configuration, and with an enlargement of the tissue gripping features.

FIGS. 6-7 show an exemplary variation of compression devices (100, 200). In particular, this variation of compression devices (100, 200) comprises contact surfaces (132, 232) that have tissue gripping features (134, 234) along first collapsible arm (112, 212) and second collapsible arm (114, 214). While FIGS. 6-7 show only one side of this variation of compression devices (100, 200), it should be understood that the other side of this variation of compression devices (100, 200) would also have contact surfaces (132, 232) with tissue gripping features (134, 234). As depicted in FIG. 7, tissue gripping features (134, 234) of the present example are in the form of raised bumps or cleats extending from contact surface (132, 232) in order to reduce slippage of magnetic compression device (100, 200) against the tissue at the anastomosis site.

C. Exemplary Magnetic Compression Device with Degradable Tab

Figure 8:
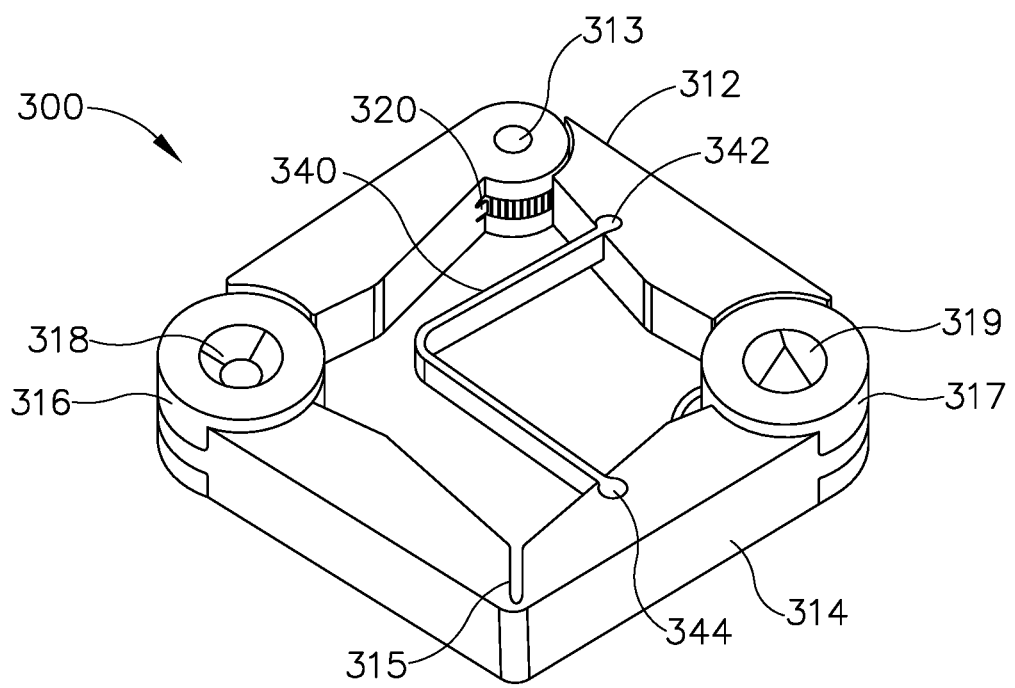
FIG. 8 depicts a perspective view of another exemplary alternative anastomosis compression device, in a wide configuration.

FIG. 8 shows another exemplary alternative magnetic anastomosis compression device (300). Magnetic anastomosis compression device (300), similar to magnetic compression devices (100, 200), comprises a first collapsible arm (312) and a second collapsible arm (314). Collapsible arms (312, 314) are pivotably connected at a first joint (316) and at a second joint (317). First collapsible arm (312) and second collapsible arm (314) are configured to transition between a wide, expanded state (see FIG. 8) and a narrow, collapsed state (similar to what is shown in FIGS. 3B and 5B) about joints (316, 317). First joint (316) further comprises a magnet (318) that is sized and shaped to have a concave configuration, recessed within first joint (316). Similarly, second joint (317) further comprises a magnet (319) that is sized and shaped to have a convex configuration, protruding from second joint (317). The protruding shape of magnet (319) is configured to associate with the corresponding recessed shape of magnet (318). Magnets (318, 319) are oriented such that concave magnet (318) presents a first magnetic pole (e.g., north) and convex magnet (319) presents a second magnetic pole (e.g., south).

Magnetic compression device (300) further comprises a mid-joint (313) positioned along first collapsible arm (312) between first joint (316) and second joint (317), such that mid-joint (313) provides a pivotal connection between segments of first collapsible arm (312). Second collapsible arm (314) comprises a living hinge (315) positioned between first joint (316) and second joint (317), such that living hinge (315) provides a pivotal connection between segments of second collapsible arm (314). Mid-joint (313) of first collapsible arm (312) and living hinge (315) of second collapsible arm (314) are configured to allow for the collapsing movement of first collapsible arm (312) and second collapsible arm (314) when flexibly changing configurations about joints (316, 317) from a wide configuration (see FIG. 8) to a narrow configuration (similar to what is shown in FIGS. 3A, 5B). Although not shown, it should be understood that mid-joint (313) may be positioned along second collapsible arm (314). Similarly, living hinge (315) may be positioned on first collapsible arm (312). As will be apparent to those of ordinary skill in the art in view of the teachings herein, magnetic anastomosis compression device (300) may include multiple mid-joints (313) or living hinges (315).

Figure 9:
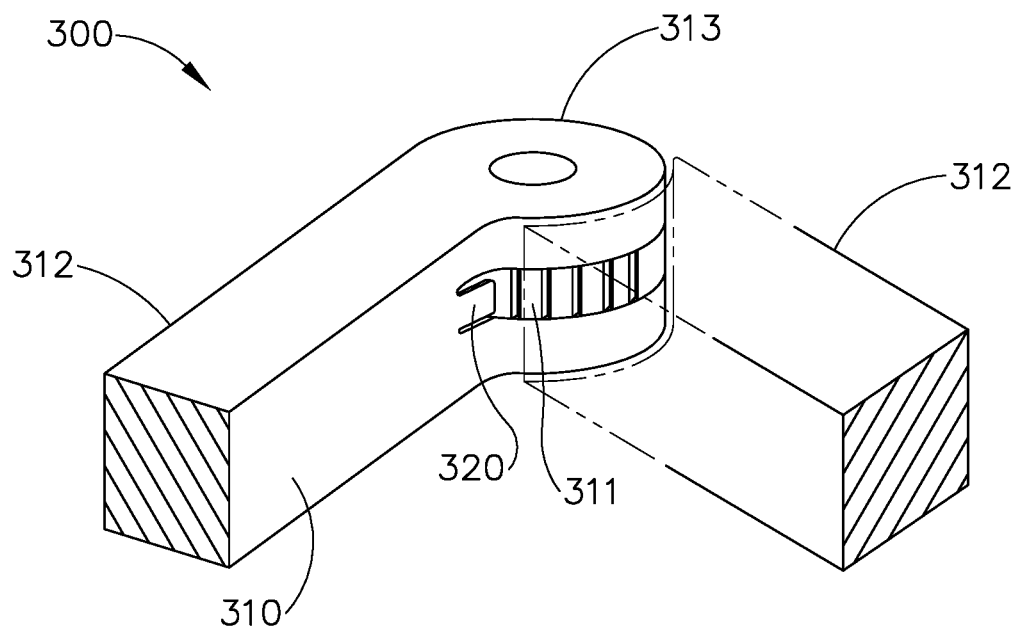
FIG. 9 depicts an enlarged partial view of the anastomosis compression device of FIG. 8, with a tab member securely fixed to a ratchet causing the device to maintain a wide configuration.

As seen in FIG. 8, magnetic compression device (300) of the present example further comprises a degradable tab (320) positioned along first collapsible arm (312) adjacent mid-joint (313). Tab (320) is formed of a degradable material in the present example. As best seen in FIG. 9, tab (320) protrudes from first collapsible arm (312) along a side plane (310) and engages a ratchet feature (311). Ratchet feature (311) is included along mid-joint (313) of first collapsible arm (312). Although not shown, it should be understood that ratchet feature (311) may be included in other locations on magnetic compression device (300) as will be apparent to those of ordinary skill in the art in view of the teachings herein, including but not limited to first joint (316) or second joint (317).

Tab (320) is configured to act as a pawl that engages teeth of ratchet feature (311), such that tab (320) and ratchet feature (311) are configured to form a ratchet assembly. This ratchet assembly is configured such that compression device (300) may substantially freely transition from a narrow, collapsed state to a wide, expanded state; yet compression device (300) may not freely transition from the wide, expanded state back to the narrow, collapsed state until tab (320) degrades as described below. Tab (320) and ratchet feature (311) thus cooperate to temporarily resist a resilient bias imposed by a spring member (340) as described below.

As seen in FIG. 8, magnetic compression device (300) further comprises a spring member (340) positioned between first collapsible arm (312) and second collapsible arm (314). Spring member (340) attaches to first collapsible arm (312) at a junction point (342) and to second collapsible arm (314) at a junction point (344). Spring member (340) is configured to resiliently bias first collapsible arm (312) and second collapsible arm (314) inwardly toward each other. The engagement between tab (320) and teeth of ratchet feature (311) resists the inward biasing force exerted by spring member (340), such that magnetic anastomosis compression device (300) remains in a wide configuration until the resistance from tab (320) is removed.

Tab (320) of the present example is formed of a degradable material such that tab (320) is configured to degrade after a predetermined amount of exposure to the gastrointestinal tract of the patient's body. Various suitable materials that may be used to form tab (320) will be apparent to those of ordinary skill in the art in view of the teachings herein. First collapsible arm (312), second collapsible arm (314), and spring member (340) are formed of a nondegradable material. While tab (320) is fully intact, magnetic compression device (300) remains in a wide configuration as seen in FIG. 8. Upon the degradation of tab (320), the ratchet assembly formed by tab (320) and ratchet feature (311) is effectively destroyed, such that the ratchet assembly no longer provides any resistance against the bias of spring member (340). The biasing force exerted by spring member (340) thus causes first collapsible arm (312) and second collapsible arm (314) to collapse inwardly toward each other thus causing magnetic compression device (300) to transition to the narrow configuration (similar to what is shown in FIGS. 3B and 5B).

The procedure of forming an anastomosis (2) by compression of two exemplary magnetic anastomosis compression devices (300) is identical to the procedure depicted in FIGS. 4A-4C for magnetic anastomosis compression device (100). It should also be understood that, while each compression device (300) is en route to the anastomosis site, each compression device (300) may be held in the narrow, contracted configuration. This may facilitate transport of compression devices (300) in a deployment instrument, through a deployment port, and/or through an enterotomy. Once each compression device (300) reaches its respective position at or near the anastomosis site, each compression device (300) may be manually transitioned to the expanded configuration of FIG. 8 (e.g., by urging joints (316, 317) toward each other). As compression device (300) is manually transitioned to the expanded configuration of FIG. 8, tab (320) will ratchet along the teeth of ratchet feature (311), such that when the operator releases compression device (300) tab (320) and ratchet feature (311) will cooperate to maintain compression device (300) In the expanded configuration.

After compression devices (300) are placed in the gastrointestinal tract of the patient, tab (320), similar to resilient band (120) of magnetic compression device (100), ultimately experiences degradation after a predetermined amount of exposure to the gastrointestinal tract of the patient's body in excess of its tolerable amount. The degradation of tab (320) of each magnetic compression device (300) causes tab (320), to dissolve and thus release the resistance force exerted by the ratchet assembly against the opposing-biasing force of spring member (340). Due to this, magnetic anastomosis compression device (300) is no longer constrained to its wide configuration as seen in FIG. 8. Spring member (340) of magnetic anastomosis compression device (300) is thereby allowed to exert its inward force upon first collapsible arms (312) and second collapsible arms (314) resulting in their collapse towards each other to a narrow configuration (similar to what is shown in FIGS. 3B and 5B). As noted above with respect to magnetic compression devices (100), magnetic compression devices (300) may thereby more easily pass through the remainder of the patient's gastrointestinal tract after detaching from the anastomosis site.

D. Exemplary Magnetic Compression Device with Degradable Tether

Figure 10:
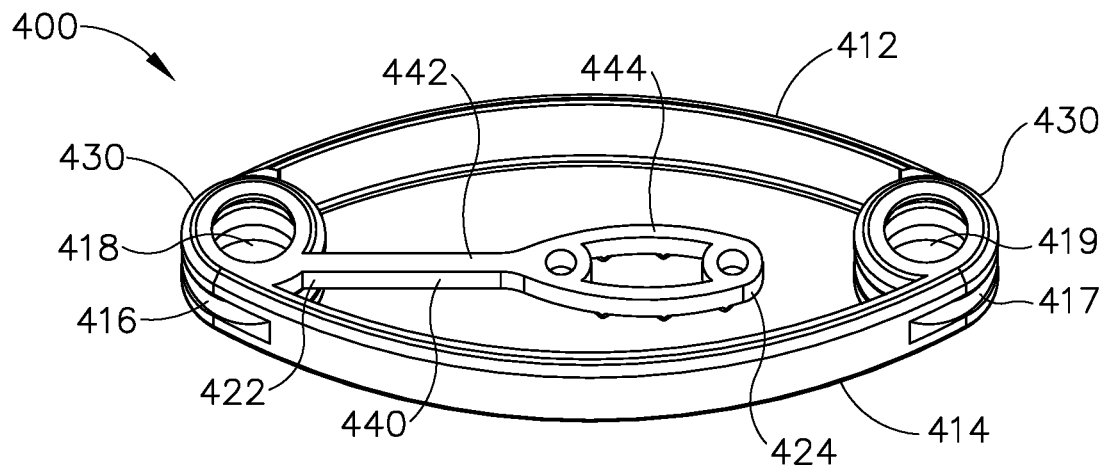
FIG. 10 depicts a perspective view of another exemplary alternative anastomosis compression device, in a narrow configuration, with a tether decoupled from an opposing end of the anastomosis compression device.

FIG. 10 shows another exemplary alternative magnetic anastomosis compression device (400). Magnetic anastomosis compression device (400) comprises a first arm (412) and a second arm (414) that are connected at a first joint (416) and a second joint (417). First arm (412) and second arm (414) each have a curved shaped and are each formed of a resilient material that provides for elastic movement of arms (412, 414) from a wide, expanded configuration (see FIG. 12A) to a narrow, contracted configuration (see FIG. 12B). The resilience of arms (412, 414) biases compression device (400) toward the narrow, contracted configuration. First joint (416) further comprises a magnet (418) that extends beyond a surface (430). Second joint (417) further comprises a magnet (419) that extends beyond a surface (430). Magnets (418, 419) are oriented such that magnet (418) presents a first magnetic pole (e.g., north) and magnet (419) presents a second magnetic pole (e.g., south).

Figure 11:
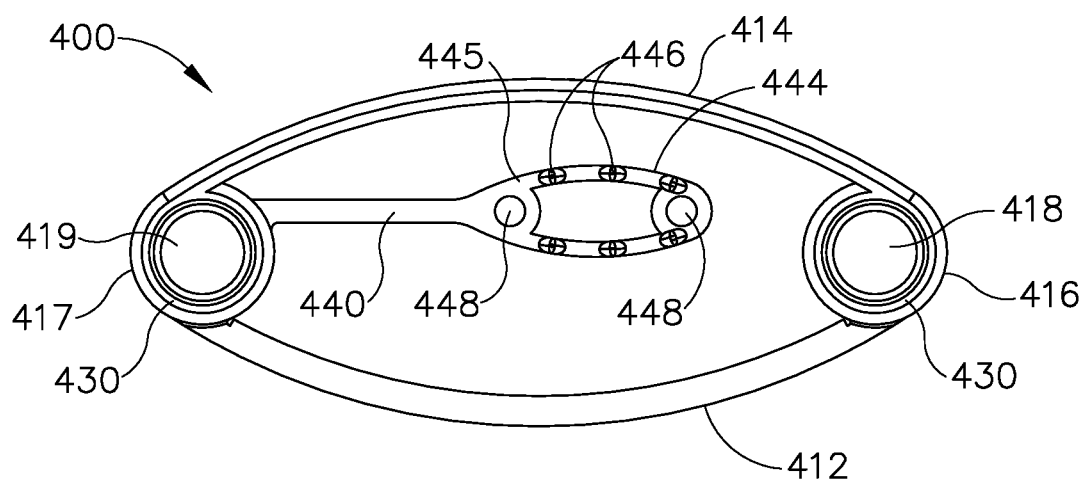
FIG. 11 depicts a bottom plan view of the anastomosis compression device of FIG. 10, with the tether decoupled from the opposing end of the anastomosis compression device.

In the present example, magnetic compression device (400) comprises a tether (440) positioned between first arm (412) and second arm (414). Tether (440) is integrally attached to first joint (416) at a proximal end (422). Tether (440) further comprises a shaft (442) extending distally from proximal end (422) and includes a receiver (444) at a distal end (424). Receiver (444) is shaped and sized to latch onto magnet (419) along the portion that extends beyond surface (430) of second joint (417). As will be apparent to those of ordinary skill in the art, tether (440) may include receiver (444) at proximal end (422) and be integrally attached to second joint (417). As best seen in FIG. 11, receiver (444) comprises grip features (446) and flex spaces (448) along a bottom surface (445) of receiver (444). Grip features (446) allow receiver (444) to securely grasp magnet (419) when tether (440) is latched onto second joint (417). Flex spaces (448) provide receiver (444) additional toggle area to latch onto magnet (419) and allows receiver (444) to adapt its size and shape accordingly. In the present example, tether (440) is non-extensible.

Figure 12A:
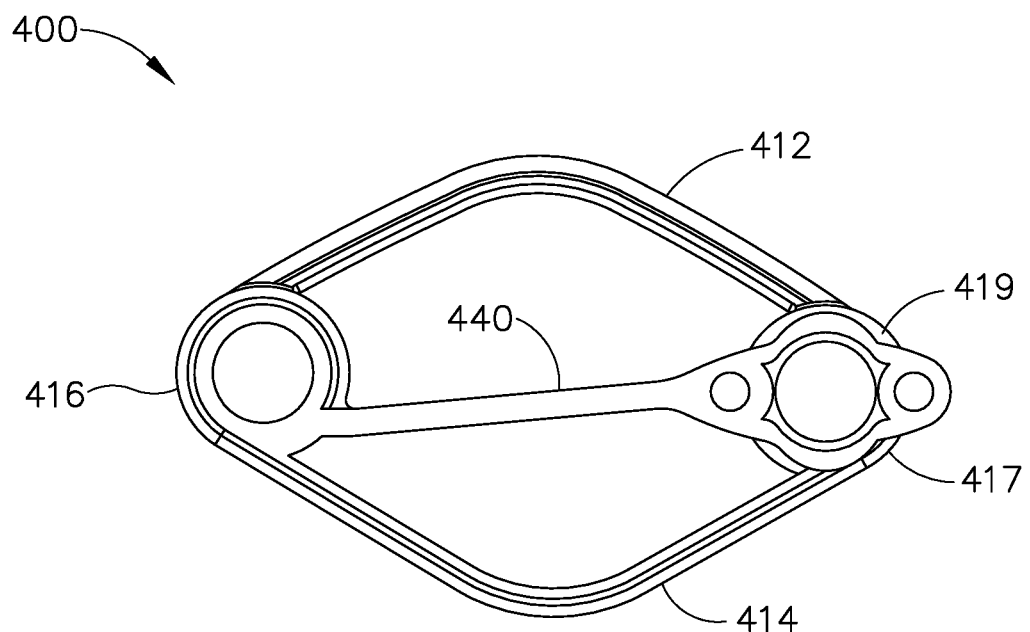
FIG. 12A depicts a top plan view of the anastomosis compression device of FIG. 10, with the tether coupled with the opposing end of the anastomosis compression device, with the anastomosis compression device in a wide configuration.
Figure 12B:
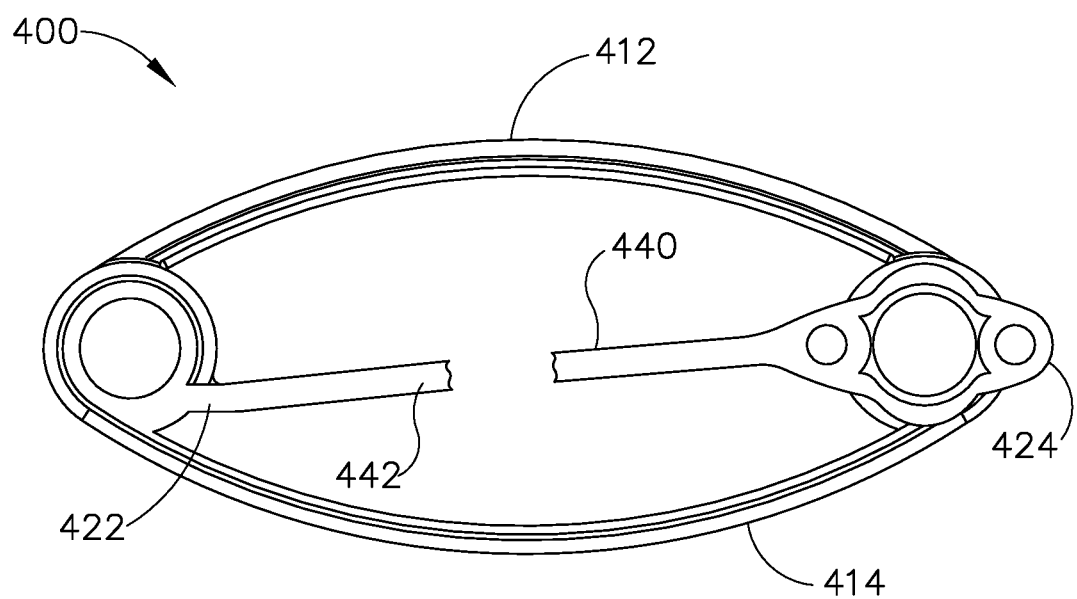
FIG. 12B depicts a top plan view of the anastomosis compression device of FIG. 10, with the tether coupled with the opposing end of the anastomosis compression device and in a degraded state, with the anastomosis compression device in a narrow configuration.

As seen in FIG. 12A, upon latching onto magnet (419) at second joint (417), tether (440) provides tension and thereby holds first arm (412) and second arm (414) in an outwardly bowed configuration, against the resilient bias of arms (412, 414) to maintain the configuration shown in FIG. 12B. Compression device (400) thus remains in a wide configuration until the resistance from tether (440) is removed.

Tether (440) of the present example is formed of a degradable material such that tether (440) is configured to degrade after a predetermined amount of exposure to the gastrointestinal tract of the patient's body. Various suitable materials that may be used to form tether (440) will be apparent to those of ordinary skill in the art in view of the teachings herein. First arm (412) and second arm (414) are formed of a nondegradable material. While receiver (444) of tether (440) is securely attached to second joint (417) and remains fully intact, magnetic compression device (400) is held in a wide configuration, as seen in FIG. 12A. Upon the degradation of tether (440) along shaft (442), tether (440) no longer provides tension to resist the resilient bias of arms (412, 414). The resilient bias of arms (412, 414) thus transitions compression device (400) to the narrow configuration.

The procedure of forming an anastomosis (2) by compression of two exemplary magnetic anastomosis compression devices (400) is identical to the procedure depicted in FIGS. 4A-4C for magnetic anastomosis compression device (100). It should also be understood that, while each compression device (400) is en route to the anastomosis site, each compression device (400) may be held in the narrow, contracted configuration. This may facilitate transport of compression devices (400) in a deployment instrument, through a deployment port, and/or through an enterotomy. Once each compression device (400) reaches its respective position at or near the anastomosis site, each compression device (400) may be manually transitioned to the expanded configuration of FIG. 12 (e.g., by urging joints (416, 417) toward each other). As compression device (400) is held in the expanded configuration of FIG. 12A, the operator may grasp receiver (444) and secure receiver (444) to magnet (419), thereby securing tension in tether (440) to hold compression device (400) in the expanded configuration against the resilient bias of arms (412, 414).

After compression devices (400) are placed in the gastrointestinal tract of the patient, tether (440), similar to resilient band (120) of magnetic compression device (100), ultimately experiences degradation in response to fluids and/or temperature conditions within the gastrointestinal tract of the patient's body. The degradation of tether (440) of each magnetic compression device (400) causes receiver (444) at distal end (424), which is securely attached to second joint (417), to detach from proximal end (422) which is integrally attached to first joint (416). The degradation of tether (440) thus removes the resistance against the opposing biasing force of first arm (412) and second arm (414). Due to this, magnetic anastomosis compression device (400) is no longer constrained to the wide configuration state as seen in FIG. 12A. As a result, first arm (412) and second arm (414) of magnetic anastomosis compression device (400) collapse toward each other as shown in FIG. 12B. As noted above with respect to magnetic compression devices (100), magnetic compression devices (400) may thereby more easily pass through the remainder of the patient's gastrointestinal tract after detaching from the anastomosis site.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A magnetic anastomosis compression assembly, comprising: (a) a first compression device, comprising: (i) a first arm, (ii) a second arm, wherein the first arm and the second arm of the first compression device are pivotably attached to each other at a pair of joints, wherein each joint of the pair of joints of the first compression device include a magnet, and (iii) a resilient member, wherein the resilient member of the first compression device is attached to the first arm and the second arm of the first compression device, wherein the resilient member of the first compression device is configured to bias the first arm and the second arm of the first compression device toward a collapsed configuration; and (b) a second compression device, comprising: (i) a first arm, (ii) a second arm, wherein the first arm and the second arm of the second compression device are pivotably attached to each other at a pair of joints, wherein each joint of the pair of joints of the second compression device include a magnet, and (iii) a resilient member, wherein the resilient member of the second compression device is attached to the first arm and the second arm of the second compression device, wherein the resilient member of the second compression device is configured to bias the first arm and the second arm toward a collapsed configuration; wherein the first compression device and the second compression device are configured to be magnetically coupled together via the magnets.

EXAMPLE 2

The anastomosis compression assembly of Example 1, wherein one of the magnets of each pair of joints comprises a convex shape, wherein the other magnet of the corresponding pair of joints comprises a concave shape.

EXAMPLE 3

The anastomosis compression assembly of any one or more of Examples 1 through 2, wherein the first and second arms of each compression device, the pair of joints of each compression device, and the resilient member of each compression device is formed of nondegradable material.

EXAMPLE 4

The anastomosis compression assembly of any one or more of Examples 1 through 3, wherein the first arm of each compression device further includes a retaining element, wherein each retaining element is configured to provide a force opposing the bias of the corresponding resilient member, wherein the force of the retaining element is greater than the opposing force of the corresponding resilient member.

EXAMPLE 5

The anastomosis compression assembly of Example 4, wherein the retaining element of each compression device is formed of degradable material.

EXAMPLE 6

The anastomosis compression assembly of Example 5, wherein the retaining element of each compression device comprises a resilient band, wherein the resilient band is received within an elongated slot positioned within a corresponding first arm of the corresponding compression device.

EXAMPLE 7

The anastomosis compression assembly of Example 5, wherein the retaining element of each compression device comprises a suture, wherein the suture is securely attached to the corresponding pair of joints of the corresponding compression device.

EXAMPLE 8

The anastomosis compression assembly of Example 5, wherein the retaining element of each compression device comprises a tab, wherein the tab is included in one of the arms of the corresponding compression device adjacent a corresponding one of the pair of joints of the corresponding compression device, wherein the each joint adjacent to the corresponding tab further includes a corresponding ratchet feature configured to receive the corresponding tab.

EXAMPLE 9

The anastomosis compression assembly of any one or more of Examples 1 through 3, wherein each compression device further includes a non-extensible tether, wherein each tether is configured to hold the corresponding compression device in an expanded configuration against the bias of the corresponding resilient member.

EXAMPLE 10

The anastomosis compression assembly of Example 9, wherein each tether includes a shaft with a proximal end and a distal end, wherein each shaft is integrally attached to one joint of the corresponding pair of joints at the proximal end, wherein each shaft includes a receiver at the distal end, wherein the receiver is configured to be secured to the corresponding opposing joint.

EXAMPLE 11

The anastomosis compression assembly of Example 10, wherein each tether comprises a degradable material.

EXAMPLE 12

The anastomosis compression assembly of any one or more of Examples 9 through 11, wherein each first arm defines a bowed configuration between the corresponding pair of joints, wherein each second arm defines a bowed configuration between the corresponding pair of joints.

EXAMPLE 13

The anastomosis compression assembly of any one or more of Examples 1 through 12, wherein the first and second compression device each include a surfaces that include tissue gripping features.

EXAMPLE 14

The anastomosis compression assembly of any one or more of Examples 1 through 13, wherein the first arm of each compression device further includes a mid-joint, wherein each mid-joint separates the corresponding first arm into a first portion and a second portion, wherein each first portion and the corresponding second portion are pivotably connected by the corresponding mid-joint.

EXAMPLE 15

The anastomosis compression assembly of any one or more of Examples 1 through 14, wherein each second arm further includes a living hinge, wherein each living hinge separates the corresponding second arm into a first portion and a second portion, wherein each first portion and the corresponding second portion are connected by the corresponding living hinge.

EXAMPLE 16

An anastomosis compression device, comprising: (a) a first collapsible leg, wherein the first collapsible leg includes a first end and a second end; (b) a second collapsible leg, wherein the second collapsible leg includes a first end and a second end; (c) a first joint pivotably coupling the first end of the first collapsible leg with the first end of the second collapsible leg; (d) a second joint pivotably coupling the second end of the second collapsible leg with the second end of the second collapsible leg, wherein the first and second collapsible legs are configured to pivot at the first and second joints to thereby transition between an expanded configuration and a contracted configuration; (e) a resilient member configured to bias the first and second collapsible legs toward the contracted configuration; and (f) a degradable member configured to maintain the first and second collapsible legs in the expanded configuration, against the bias of the resilient member.

EXAMPLE 17

The anastomosis compression assembly of Example 16, wherein the degradable member is configured to resiliently bias the first and second collapsible legs toward the expanded configuration.

EXAMPLE 18

The anastomosis compression assembly of Example 16, further comprising a ratchet assembly, wherein the ratchet assembly includes a set of teeth, wherein the degradable member comprises a pawl, wherein the pawl is configured to ratchet along the teeth of the ratchet assembly.

EXAMPLE 19

The anastomosis compression assembly of Example 16, wherein the degradable member comprises a tether extending between the first joint and the second joint.

EXAMPLE 20

An anastomosis compression device, comprising: (a) a first collapsible leg, wherein the first collapsible leg includes: (i) a first segment, and (ii) a second segment, wherein the first and second segments are pivotably coupled together; (b) a second collapsible leg, wherein the first and second collapsible legs are configured to transition between an expanded configuration and a contracted configuration, wherein the second collapsible leg includes: (i) a third segment, and (ii) a fourth segment, wherein the third and fourth segments are pivotably coupled together; (c) a first joint pivotably coupling the first segment and the third segment; (d) a second joint pivotably coupling the second segment and the fourth segment; (e) a resilient member secured to the second segment and the fourth segment, wherein the resilient member is configured to bias the first and second collapsible legs toward the contracted configuration; and (f) a degradable member configured to maintain the first and second collapsible legs in the expanded configuration, against the bias of the resilient member, wherein the degradable member is secured to either: (i) the first segment and the second segment, or (ii) the first joint and the second joint.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A magnetic anastomosis compression assembly, comprising:
   (a) a first compression device, comprising:
      (i) a first arm,
      (ii) a second arm, wherein the first arm and the second arm of the first compression device are pivotably attached to each other at a pair of joints along a single pivot axis at each joint of the pair of joints, wherein each joint of the pair of joints of the first compression device includes a magnet, and
      (iii) a resilient member, wherein the resilient member of the first compression device is attached to the first arm and the second arm of the first compression device, wherein the resilient member of the first compression device is configured to bias the first arm and the second arm of the first compression device toward a collapsed configuration; and
   (b) a second compression device, comprising:
      (i) a first arm,
      (ii) a second arm, wherein the first arm and the second arm of the second compression device are pivotably attached to each other at a pair of joints along a single pivot axis at each joint of the pair of joints, wherein each joint of the pair of joints of the second compression device includes a magnet, and
      (iii) a resilient member, wherein the resilient member of the second compression device is attached to the first arm and the second arm of the second compression device, wherein the resilient member of the second compression device is configured to bias the first arm and the second arm toward a collapsed configuration;
   wherein the first compression device and the second compression device are configured to be magnetically coupled together via the magnets.

2. The anastomosis compression assembly of claim 1, wherein one of the magnets of each pair of joints comprises a convex shape, wherein the other magnet of the corresponding pair of joints comprises a concave shape.

3. The anastomosis compression assembly of claim 1, wherein the first and second arms of each compression device, the pair of joints of each compression device, and the resilient member of each compression device is formed of nondegradable material.

4. The anastomosis compression assembly of claim 1, wherein the first arm of each compression device further includes a retaining element, wherein each retaining element is configured to provide a force opposing the bias of the corresponding resilient member, wherein the force of the retaining element is greater than the opposing force of the corresponding resilient member.

5. The anastomosis compression assembly of claim 4, wherein the retaining element of each compression device is formed of degradable material.

6. The anastomosis compression assembly of claim 5, wherein the retaining element of each compression device comprises a resilient band, wherein the resilient band is received within an elongated slot positioned within a corresponding first arm of the corresponding compression device.

7. The anastomosis compression assembly of claim 5, wherein the retaining element of each compression device is configured to degrade within the gastrointestinal tract of a patient while the remaining portion of the compression assembly remains intact.

8. The anastomosis compression assembly of claim 5, wherein each of the first and second compression devices is configured to assume the collapsed configuration in response to degradation of the respective retaining element.

9. The anastomosis compression assembly of claim 4, wherein the retaining element further comprises multiple resilient bands.

10. The anastomosis compression assembly of claim 1, wherein the first and second compression device each include a surface that includes tissue gripping features.

11. The anastomosis compression assembly of claim 1, wherein the first arm of each compression device further includes a mid-joint, wherein each mid-joint separates the corresponding first arm into a first portion and a second portion, wherein each first portion and the corresponding second portion are pivotably connected by the corresponding mid-joint.

12. The anastomosis compression assembly of claim 1, wherein each second arm further includes a living hinge, wherein each living hinge separates the corresponding second arm into a first portion and a second portion, wherein each first portion and the corresponding second portion are connected by the corresponding living hinge.

13. The anastomosis compression assembly of claim 1, wherein the second arm of each compression device further includes a retaining element, wherein each retaining element is configured to provide a force opposing the bias of the corresponding resilient member, wherein the force of the retaining element is greater than the opposing force of the corresponding resilient member.

14. The anastomosis compression assembly of claim 1, wherein the resilient members are formed of degradable material, wherein each of the first and second compression devices is configured to assume the collapsed configuration in response to degradation of the respective resilient members.

15. The anastomosis compression assembly of claim 14, wherein the first arm and the second arm of the first compression device are configured be biased toward a collapsed configuration by an inner wall of a gastrointestinal tract of a patient's body upon degradation of the resilient member.

16. An anastomosis compression device, comprising:
(a) a first collapsible leg, wherein the first collapsible leg includes a first end and a second end;
(b) a second collapsible leg, wherein the second collapsible leg includes a first end and a second end;
(c) a first joint pivotably coupling the first end of the first collapsible leg with the first end of the second collapsible leg;
(d) a second joint pivotably coupling the second end of the first collapsible leg with the second end of the second collapsible leg, wherein the first and second collapsible legs share a pivot at each of the first and second joints, wherein the first and second collapsible legs are configured to pivot at the first and second joints to thereby transition between an expanded configuration and a contracted configuration;
(e) a resilient member configured to bias the first and second collapsible legs toward the contracted configuration; and
(f) a degradable member configured to maintain the first and second collapsible legs in the expanded configuration, against the bias of the resilient member.

17. The anastomosis compression assembly of claim 16, wherein the degradable member is configured to resiliently bias the first and second collapsible legs toward the expanded configuration.

18. The anastomosis compression assembly of claim 16, wherein the degradable member comprises multiple resilient bands.

19. The anastomosis compression assembly of claim 16, wherein the degradable member of the compression device is configured to degrade within the gastrointestinal tract of a patient while the remaining portion of the compression assembly remains intact.

20. An anastomosis compression device, comprising:
(a) a first collapsible leg, wherein the first collapsible leg includes:
(i) a first segment, and
(ii) a second segment, wherein the first and second segments are pivotably coupled together;
(b) a second collapsible leg, wherein the first and second collapsible legs are configured to transition between an expanded configuration and a contracted configuration, wherein the second collapsible leg includes:
(i) a third segment, and
(ii) a fourth segment, wherein the third and fourth segments are pivotably coupled together;
(c) a first joint pivotably coupling the first segment and the third segment;
(d) a second joint pivotably coupling the second segment and the fourth segment, wherein an exterior surface of the first and second collapsible legs define an outer boundary of the anastomosis compression device;
(e) a resilient member secured to the second segment and the fourth segment, wherein the resilient member is positioned within the outer boundary, wherein the resilient member is configured to bias the first and second collapsible legs toward the contracted configuration; and
(f) a degradable member configured to maintain the first and second collapsible legs in the expanded configuration, against the bias of the resilient member, wherein the degradable member is secured to either:
(i) the first segment and the second segment, or
(ii) the first joint and the second joint.

* * * * *